(12) United States Patent
Greene et al.

(10) Patent No.: US 6,815,168 B1
(45) Date of Patent: Nov. 9, 2004

(54) HUMAN PEROXISOME PROLIFERATOR ACTIVATED RECEPTOR γ COMPOSITIONS AND METHODS

(76) Inventors: Marianne E. Greene, 2020 Lincoln Park West Apt. 17G, Chicago, IL (US) 60614; Bruce Blumberg, 3435 Lebon Dr. #1122, San Diego, CA (US) 92122

( * ) Notice: Subject to any disclaimer, the term of this patent is extended or adjusted under 35 U.S.C. 154(b) by 467 days.

(21) Appl. No.: 09/587,549

(22) Filed: Jun. 1, 2000

Related U.S. Application Data

(62) Division of application No. 08/134,557, filed on Oct. 8, 1993, now Pat. No. 6,200,802.

(51) Int. Cl.[7] .................. G01N 33/53; C12N 15/00; C12N 1/20
(52) U.S. Cl. .................. 435/7.1; 435/325; 435/252.33
(58) Field of Search .................. 435/7.1, 325, 252.33

(56) References Cited

U.S. PATENT DOCUMENTS 5,861,274 A    1/1999  Evans et al.

OTHER PUBLICATIONS

Gottlicher et al., Proc. Natl. Acad. Sci. USA 89: pp. 4653–4657 (1992).*
Isseman et al., Nature vol. 347: pp. 645–650 (1990).*
Dreyer, Christine, et al., "Control of the Peroxisomal β–oxidation Pathway by a Novel Family of Nuclear Hormone Receptors", *Cell*, 68:879–887, (1992).
Schmidt, Azriel, et al., "Identification of a New Member of the Steroid Hormone Receptor Superfamile That is Activated by a Peroxisome Proliferator and Fatty Acids", *Mol. Endo.*, 6(4):1634–1641, (1992).
Sher, Talia, et al., "cDNA Cloning Chromosomal Mapping and Functional Characterization of the Human Peroxisome Proliferator Activated Receptor", *Biochemistry*, 32:5598–5604. (1993).

* cited by examiner

*Primary Examiner*—Terry McKelvey
*Assistant Examiner*—Nancy Vogel

(57) ABSTRACT

The invention relates generally to compositions of and methods for obtaining peroxisome proliferator-activated receptors. The invention relates as well to the DNA sequences encoding peroxisome proliferator-activated receptors, the recombinant vectors carrying those sequences, the recombinant host cells including either the sequences or vectors, and recombinant peroxisome proliferator-activated receptor polypeptides. By way of example, the invention discloses the cloning and functional expression of a peroxisome proliferator-activated receptor, designated PPAR-γ, obtained from a human source. The invention includes as well, methods for using the isolated, recombinant peroxisome proliferator-activated receptor polypeptides in assays designed to select and improve substances capable of interacting with peroxisome proliferator-activated receptor polypeptides for use in diagnostic, drug design and therapeutic applications.

31 Claims, 1 Drawing Sheet

AMINO ACID IDENTITY AMONG MEMBERS OF THE PPAR FAMILY

| | A/B | C | D | E | |
|---|---|---|---|---|---|
| hPPAR γ | 110 | 175 | 253 | T1 | 479 |
| xPPAR γ | 57% / 112 | 97% / 177 | 70% / 257 | 90% / 91% | 477 |
| xPPAR α | 15% / 108 | 84% / 173 | 59% / 250 | 7% / 77% / 75% | 474 |
| xPPAR β | 2% / 30 | 74% / 95 | 51% / 171 | 30% / 24% / 71% | 396 |
| mPPAR α | 14% / 102 | 83% / 166 | 57% / 244 | 31% / 82% / 72% | 468 |
| hPPAR α | 14% / 102 | 83% / 166 | 58% / 244 | 35% / 74% / 72% | 468 |
| hNUC 1 | 3.5% / 72 | 83% / 138 | 59% / 215 | 26% / 74% / 77% | 441 |
| hRAR α | 11.5% / 87 | 65% / 156 | 19.5% / 224 | 4.7% / 36% / 28% | 462 | key: h= human  m=murine  x=xenopus

FIG. 1

HUMAN PEROXISOME PROLIFERATOR ACTIVATED RECEPTOR γ COMPOSITIONS AND METHODS

RELATED APPLICATION

This application is a divisional application of U.S. Ser. No. 08/134,557, filed Oct. 8, 1993 now U.S. Pat. No. 6,200,802.

FIELD OF THE INVENTION

This invention relates generally to compositions of and methods for obtaining peroxisome proliferator-activated receptorγ polypeptides. The invention relates as well to the DNA sequences encoding these receptor polypeptides, the recombinant vectors carrying those sequences, the recombinant host cells including either the sequences or vectors, and recombinant peroxisome proliferator-activated receptorγ polypeptides. The invention includes, as well, methods for using the isolated, recombinant receptor polypeptides in assays designed to select and peroxisome proliferator-activated receptor-γ polypeptides for use in diagnostic, drug design and therapeutic applications.

BACKGROUND OF THE INVENTION

The steroid hormone (or nuclear) receptor superfamily has many is members that play important roles in regulating cancer cells, including, but not limited to, the estrogen receptor (Bettuzi, 1991), the retinoic acid receptors (Menger, 1988), and v-erb A (Sharif, 1991). A number of less well characterized members of this family have been isolated and identified based on their homology to the better known nuclear receptors. (Laudet, 1992). Many show ligand-dependent activation patterns, but the identity of natural ligands that control these transcription factors is still unknown, or under investigation. Members of the steroid hormone receptor family whose ligands have not yet been identified are referred to as "orphan" receptors. The full importance of these "orphan" receptors is predicted by their presence early in development and by the fact that many (including PPAR, COUP, ROR) have been shown to interact with the known members of the superfamily (Beck, 1992; O'Malley, 1992; Tsukiyama, 1992). Many of these receptors are undoubtedly important in regulating cell growth and response to the environment, and may well have regulatory roles in cancer cells, like their currently well-studied counterparts.

The present invention provides a novel "orphan" receptor polypeptide, the human Peroxisome Proliferator Receptor γ (hPPAR-γ). It is a member of a group of orphan receptors found to be activated (but not bound) by arachidonic acid, fatty acids, clofibrate, and other agents that induce the proliferation of peroxisomes in rodents. (Blaauboer, 1990).

Peroxisome proliferators are a diverse group of chemicals which include hypolipidemic drugs, herbicides, leukotriene antagonists, and plasticizers. Two major categories of peroxisome proliferator chemicals play a significant role in society today. The first, the fibrate class of hypolipidemic drugs, has been found to be effective at reducing the levels of triglycerides and cholesterol in humans suffering from hyperlipidemia, a major risk factor for heart disease (Berioli, 1990). The second category relates to phthalate ester plasticizers used in the production of highly versatile flexible vinyl plastics (Reddy, 1983).

Peroxisome proliferators seem to affect most mammalian species that have been tested. They induce hepatomegaly resulting from liver hyperplasia and an increase in the size and number of peroxisomes. (Reddy, 1983.) Nevertheless, on the basis of hypolipidemic drug dose required to produce recognizable peroxisome proliferation, mice and rats are considered to be highly responsive to these agents, developing hepatocellular carcinoma following long-term drug administration; hamsters have intermediate responses; and guinea pigs, marmosets and other nonhuman primates are weakly responsive (Eacho, 1986).

Peroxisome proliferators are termed non-genotoxic carcinogens as they fail to cause DNA damage directly (Warren, 1980). The increase in peroxisomal fatty acid β-oxidation seen in response to peroxisome proliferators results in a greater production of hydrogen peroxide. It has been proposed that this results in oxidative stress leading to DNA damage and possible tumor initiation. (Reddy, 1983; Kasai, 1989). Alternatively, or in addition, peroxisome proliferators may act as liver-tumor promoters. (Marsman, 1988; Cattley, 1989).

The nuclear receptor subfamily to which the receptor polypeptide of the present invention belongs has been shown to regulate the transcription of several key enzymes in fatty acid metabolism, including Acyl Co A oxidase (Tugwood, 1992), and CYP4A6, a cytochrome P-450 omega hydroxylase, potentially having profound effects upon host responses via leukotriene and prostaglandin catabolism, fatty acid β oxidation, and superoxide production. Host response is a key aspect to the pathology of all diseases, including cancer, infection, and autoimmune disorders.

Recent studies demonstrate the PPARs can heterodimerize with the 9-cis retinoic acid receptor (RXR) and synergistically induce gene expression (Kliewer, 1992). These studies demonstrate a potential link between the retinoid responsive pathways and the lipid/arachidonic acid metabolic pathways. Preservation of the hydrophobic heptad repeats in the dimerization domain (see discussion below) indicates that PPARs can heterodimerize with other members of the thyroid/retinoid subbranch of the superfamily containing these repeats. There is also some conservation of the "conserved activating motif" (Daneilian et al., 1992) in the carboxy terminus.

PPARs are orphan receptors described in the murine (Issemann, 1990), rat (Gottlicher, 1992), human (Sher, 1993) and xenopus systems (Dreyer, 1992) as the peroxisome proliferator activated receptors α, β, and γ. A fourth member (h NUC 1) with some interesting unique sequence characteristics was isolated from human osteosarcoma cells (Schmidt, 1992). These receptors in other species are known to be activated by arachidonic acid at 150 μM levels, long chain fatty acids such as oleic and petroselenic acid, clofibrate, and other peroxisome proliferating agents (Gottlicher, 1992; Isseman, 1990). Arachidonic acid can trigger many different responses in cells such as neutrophils, but PPAR activation by long chain fatty acids provides evidence that arachidonic acid metabolites are candidate ligands or activators. In addition, murine PPAR-α has been shown to transactivate as a heterodimer with the human Retinoid X Receptor alpha (hRXR-α) both on retinoid receptor targets as well as on known PPAR target promoter sequences, potentially linking these pathways of gene regulation (Kliewer, 1992).

PPARs may play a role in proliferative and differentiation aspects of cancer, because they have also been shown to be developmentally active in vertebrates (xenopus), and are present in oocytes, fertilized eggs, blastulae, gastrulae, neurulae, and early tadpoles (Dreyer, 1992). It should be noted that many other members of the nuclear receptor superfamily appear to have two sets of regulatory functions. The first occurs during embryogenesis and development, including axis and pattern formation (Blumberg, 1992), and the second occurs in the adult, where the receptors modulate transcriptional activities in response to neighboring cells, other tissues, and aspects of the environment, particularly on regenerating tissues (Elder, 1991; Howell, 1990).

Members of the superfamily of nuclear hormone receptors have also been shown to directly connect the cellular transcriptional response to extracellular signals such as retinoids and steroids, as well as fatty acid and arachidonic acid metabolites, as already mentioned (Aronica, 1991). Studies of these receptors in hematopoiesis have primarily focused upon the retinoic acid receptor alpha (RAR-α) and v-erb A genes because of their important effects on hematopoietic cell differentiation.

The retinoic acid receptor α gene on chromosome 17 is translocated to chromosome 15 in virtually all cases of human acute promyelocytic leukemia (APL) (Rowley, 1988), where it is fused with PML gene. This generates two fusion proteins, containing RAR-α and PML sequences, which have different transcriptional activating properties than the wild type proteins. Treatment of APL patients with the ligand, all trans retinoic acid, consistently results in the achievement of a complete remission in this disease (Menger, 1988).

V-erb A is an aberrant version of a thyroid hormone receptor that can block erythroid differentiation and induce malignant transformation, an ability that is correlated with the repression of retinoic acid receptor function. Both retinoic acid receptors and v-erb A elicit significant effects upon the hematopoietic system by interacting with other transcription factors, such as fos and jun (Schule, 1991), and with other related nuclear receptors leading to heterodimer formation (Debois, 1991). The retinoic acid receptors, (RARs) can heterodimerize with retinoid x receptors (RXRs) in vitro, which increases their affinity for the RAR response element. RXRs can also heterodimerize with a number of different members of the superfamily in vitro, including the PPARs (Kliewer, 1992).

Target genes identified as transcriptionally activated by PPARs include acyl co-A oxidase, the key enzyme regulating the fatty acid B oxidation pathway (Tugwell, 1992), and CYP4A6, a cytochrome P450 fatty acid ω hydroxylase, a key enzyme catalyzing the ω hydroxylation of arachidonic, lauric and palmitic acids (Muerhoff, 1992). The sequence in the rat acyl-Co A oxidase promoter bound by PPARs is "acgTGACCTtTGTCCTggt" (SEQ ID NO:6) (Tugwell, 992), which contains a direct repeat, separated by one nucleotide, ("DR-1" motif) (Umesono, 1991) of the canonical consensus half site "TGACCT" (SEQ ID NO:7) to which all members of the thyroid-retinoid branch of the nuclear receptor superfamily can bind (Laudet 1992). The target sequences in CYP4A6 appear as imperfect DR-1 motifs and more complex arrangements of imperfect half sites. Candidate gene promoters must be tested for PPAR activation, but genes such as CD18, the leukocyte integrin β subunit, which has multiple combinations of imperfect half-sites and is retinoic acid inducible (Agura, 1992), are possibly PPAR responsive. Catalase, hydroxyacid oxidase, and uricase are down regulated by peroxisome proliferators in the rat, under the same conditions that up regulate acyl-coA oxidase. The effects of PPAR upon myeloperoxidase, chloroacetate esterase or catalase in myeloid cells have not been examined. Further characterization of these two forms of the PPAR-γ mRNA will be extremely useful for understanding their functions in hematopoietic cells as well as other organ systems.

SUMMARY OF THE INVENTION

In one aspect, the present invention provides an isolated and purified polynucleotide that encodes a peroxisome proliferator-activated receptor polypeptide. In a preferred embodiment, a polynucleotide of the present invention is a DNA molecule. More preferably, a polynucleotide of the present invention encodes a polypeptide that is a peroxisome proliferator-activated receptor-γ. Even more preferred, a polynucleotide of the present invention encodes a polypeptide comprising the amino acid residue sequence of SEQ ID NO:2. Most preferably, an isolated and purified polynucleotide of the invention comprises the nucleotide base sequence of SEQ ID NO:1.

In an alternative aspect, the present invention contemplates an isolated and purified polynucleotide that encodes a peroxisome proliferator-activated receptor polypeptide, said polynucleotide preparable by a process comprising the steps of (a) constructing a library of cDNA clones from a cell that expresses said polypeptide; (b) screening the library with a radio-labelled oligonucleotide probe; (c) identifying a clone that hybridizes to the probe; and (d) isolating the hybridized clone from the library of unhybridized clones. Preferably, the present invention provides an isolated and purified polynucleotide that encodes a peroxisome proliferator-activated receptor polypeptide prepared by a process comprising the steps of (a) constructing a library of cDNA clones from a cell that expresses said polypeptide; (b) screening the library with a radio-labelled oligonucleotide probe; (c) identifying a clone that hybridizes to the probe; and (d) isolating the hybridized clone from the library of unhybridized clones. More preferably, the polypeptide encoded has the amino acid residue sequence of SEQ ID NO: 2. Still more preferably, the polynucleotide comprises the nucleotide sequence of SEQ ID NO: 1.

Yet another aspect of the present invention contemplates an isolated and purified polynucleotide comprising a base sequence that is identical or complementary to a segment of at least 10 contiguous bases of SEQ ID NO: 1, wherein the polynucleotide hybridizes to a polynucleotide that encodes a peroxisome proliferator-activated receptor polypeptide. Preferably, the isolated and purified polynucleotide comprises a base sequence that is identical or complementary to a segment of at least 25 to 70 contiguous bases of SEQ ID NO: 1. For example, the polynucleotide of the present invention can comprise a segment of nucleotide bases identical or complementary to 40 or 55 contiguous bases of the disclosed nucleotide sequences.

In still another embodiment of the present invention, there is provided an isolated and purified polynucleotide comprising a base sequence that is identical or complementary to a segment of at least 10 contiguous bases of SEQ ID NO: 1. The polynucleotide of the invention hybridizes to SEQ ID NO: 1, or a complement of SEQ ID NO: 1. Preferably, the isolated and purified polynucleotide comprises a base sequence that is identical or complementary to a segment of at least 25 to 70 contiguous bases of SEQ ID NO: 1. For example, the polynucleotide of the invention can comprise a segment of bases identical or complementary to 40 or 55 contiguous bases of SEQ ID NO: 1.

In another embodiment, the present invention contemplates an isolated and purified peroxisome proliferator-activated receptor polypeptide. Preferably, a peroxisome proliferator-activated receptor polypeptide of the invention is a recombinant polypeptide. More preferably, a peroxisome proliferator-activated receptor polypeptide of the present invention is a peroxisome proliferator-activated receptor-γ polypeptide. Even more preferably, a peroxisome proliferator-activated receptor polypeptide of the present invention comprises the amino acid residue sequence of SEQ ID NO:2.

In an alternative embodiment, the present invention provides an expression vector comprising a polynucleotide that encodes a peroxisome proliferator-activated receptor polypeptide. Preferably, an expression vector of the present invention comprises a polynucleotide that encodes a polypeptide comprising the amino acid residue sequence of SEQ ID NO:2. More preferably, an expression vector of the present invention comprises a polynucleotide comprising the nucleotide base sequence of SEQ ID NO:1. Even more preferably, an expression vector of the invention comprises a polynucleotide operatively linked to an enhancer-promoter. More preferably still, an expression vector of the invention comprises a polynucleotide operatively linked to a prokaryotic promoter. Alternatively, an expression vector of the present invention comprises a polynucleotide operatively linked to an enhancer-promoter that is a eukaryotic promoter, and the expression vector further comprises a polyadenylation signal that is positioned 3' of the carboxy-terminal amino acid and within a transcriptional unit of the encoded polypeptide.

In yet another embodiment, the present invention provides a recombinant host cell transfected with a polynucleotide that encodes a peroxisome proliferator-activated receptor polypeptide. Preferably, a recombinant host cell of the present invention is transfected with the polynucleotide of SEQ ID NO:1. Even more preferably, a host cell of the invention is a eukaryotic host cell. Still more preferably, a recombinant host cell of the present invention is a yeast cell. Alternatively, a recombinant host cell of the invention is a COS-1 cell. In another aspect, a recombinant host cell of the present invention is a prokaryotic host cell.

In yet another embodiment, the present invention contemplates a process of preparing a peroxisome proliferator-activated receptor polypeptide comprising transfecting a cell with polynucleotide that encodes a peroxisome proliferator-activated receptor polypeptide to produce a transformed host cell; and maintaining the transformed host cell under biological conditions sufficient for expression of the polypeptide. Preferably, the transformed host cell is a eukaryotic cell. More preferably still, the eukaryotic cell is a COS-1 cell. Alternatively, the host cell is a prokaryotic cell. More preferably, the prokaryotic cell is a bacterial cell of the DH5α strain of *Escherichia coli*. Even more preferably, a polynucleotide transfected into the transformed cell comprises the nucleotide base sequence of SEQ ID NO:1.

In still another embodiment, the present invention provides an antibody immunoreactive with a peroxisome proliferator-activated receptor polypeptide. Preferably, an antibody of the invention is a monoclonal antibody. More preferably, the antibody is immunoreactive with a peroxisome proliferator-activated receptor polypeptide that comprises the amino acid residue sequence of SEQ ID NO:2.

In another aspect, the present invention contemplates a process of producing an antibody immunoreactive with a peroxisome proliferator-activated receptor polypeptide comprising the steps of (a) transfecting a recombinant host cell with a polynucleotide that encodes a peroxisome proliferator-activated receptor polypeptide; (b) culturing the host cell under conditions sufficient for expression of the polypeptide; (c) recovering the polypeptide; and (d) preparing the antibody to the polypeptide. Preferably, the host cell is transfected with the polynucleotide of SEQ ID NO:1.

Even more preferably, the present invention provides an antibody prepared according to the process described above.

Alternatively, the present invention provides a process of detecting a peroxisome proliferator-activated receptor polypeptide, wherein the process comprises immunoreacting the polypeptide with an antibody prepared according to the process described above to form an antibody-polypeptide conjugate, and detecting the conjugate.

In yet another embodiment, the present invention contemplates a process of detecting a messenger RNA transcript that encodes a peroxisome proliferator-activated receptor polypeptide, wherein the process comprises (a) hybridizing the messenger RNA transcript with a polynucleotide sequence that encodes the peroxisome proliferator-activated receptor polypeptide to form a duplex; and (b) detecting the duplex. Alternatively, the present invention provides a process of detecting a DNA molecule that encodes a peroxisome proliferator-activated receptor polypeptide, wherein the process comprises (a) hybridizing DNA molecules with a polynucleotide that encodes a peroxisome proliferator-activated receptor polypeptide to form a duplex; and (b) detecting the duplex.

Alternatively, the present invention contemplates a pharmaceutical composition comprising a peroxisome proliferator-activated receptor polypeptide and a physiologically acceptable carrier. Preferably, the present invention provides a pharmaceutical composition comprising a receptor polypeptide that comprises the amino acid residue sequence of SEQ ID NO:2. In another embodiment, the present invention provides a pharmaceutical composition comprising a polynucleotide that encodes a peroxisome proliferator-activated receptor polypeptide, and a physiologically acceptable carrier. Preferably, that pharmaceutical composition comprises a polynucleotide encoding a receptor polypeptide comprising the amino acid residue sequence of SEQ ID NO:2. Even more preferably, the pharmaceutical composition comprises a polynucleotide that comprises the nucleotide sequence of SEQ ID NO:1.

In another aspect, the present invention contemplates a diagnostic assay kit for detecting the presence of a peroxisome proliferator-activated receptor polypeptide in a biological sample, where the kit comprises a first container containing a first antibody capable of immunoreacting with a peroxisome proliferator-activated receptor polypeptide, with the first antibody present in an amount sufficient to perform at least one assay. Preferably, an assay kit of the invention further comprises a second container containing a second antibody that immunoreacts with the first antibody. More preferably, the antibodies used in an assay kit of the present invention are monoclonal antibodies. Even more preferably, the first antibody is affixed to a solid support. More preferably still, the first and second antibodies comprise an indicator, and, preferably, the indicator is a radioactive label or an enzyme.

In an alternative aspect, the present invention provides a diagnostic assay kit for detecting the presence, in biological samples, of a polynucleotide that encodes a peroxisome proliferator-activated receptor polypeptide, the kits comprising a first container that contains a second polynucleotide identical or complementary to a segment of at least 10 contiguous nucleotide bases of SEQ ID NO:1.

In another embodiment, the present invention contemplates a diagnostic assay kit for detecting the presence, in a biological sample, of an antibody immunoreactive with a peroxisome proliferator-activated receptor polypeptide, the kit comprising a first container containing a peroxisome proliferator-activated receptor polypeptide that immunoreacts with the antibody, with the polypeptide present in an amount sufficient to perform at least one assay.

In yet another aspect, the present invention contemplates a process of screening substances for their ability to interact with a peroxisome proliferator-activated receptor polypeptide comprising the steps of providing a peroxisome proliferator-activated receptor polypeptide, and testing the ability of selected substances to interact with the peroxisome proliferator-activated receptor polypeptide.

In a preferred embodiment, providing a peroxisome proliferator-activated receptor polypeptide is transfecting a host cell with a polynucleotide that encodes a peroxisome proliferator-activated receptor polypeptide to form a transformed cell and maintaining the transformed cell under biological conditions sufficient for expression of the peroxisome proliferator-activated receptor polypeptide.

BRIEF DESCRIPTION OF THE DRAWING

FIG. 1: Comparative amino acid identity between hPPAR-γ, other members of the PPAR family, and hRAR α. The percentage of amino acid identity among the various receptors and hPPAR-γ is indicated for each domain. The E domain is further subdivided to indicate the location of the highly conserved τ 1 putative silencing domain (Forman and Samuels, 1990).

DETAILED DESCRIPTION OF THE INVENTION

I. The Invention

The present invention provides DNA segments, purified polypeptides, methods for obtaining antibodies, methods of cloning and using recombinant host cells necessary to obtain and use recombinant peroxisome proliferator-activated receptors. Thus, the difficulties encountered with applying the standard approaches of classical genetics or techniques in molecular biology evident in the prior art to peroxisome proliferator-activated receptors, have been overcome. Accordingly, the present invention concerns, generally, compositions and methods for the preparation and use of peroxisome proliferator-activated receptors.

II. Polynucleotides

A. Isolated and Purified Polynucleotides that Encode Peroxisome Proliferator-activated Receptor Polypeptides.

In one aspect, the present invention provides an isolated and purified polynucleotide that encodes a peroxisome proliferator-activated receptor polypeptide. In a preferred embodiment, a polynucleotide of the present invention is a DNA molecule. More preferably, a polynucleotide of the present invention encodes a polypeptide that is a peroxisome proliferator-activated receptor-γ. Even more preferred, a polynucleotide of the present invention encodes a polypeptide comprising the amino acid residue sequence of SEQ ID NO:2. Most preferably, an isolated and purified polynucleotide of the invention comprises the nucleotide base sequence of SEQ ID NO:1.

As used herein, the term "polynucleotide" means a sequence of nucleotides connected by phosphodiester linkages. Polynucleotides are presented herein in the direction from the 5' to the 3' direction. A polynucleotide of the present invention can comprise from about 680 to about several hundred thousand base pairs. Preferably, a polynucleotide comprises from about 680 to about 150,000 base pairs. Preferred lengths of particular polynucleotide are set forth hereinafter.

A polynucleotide of the present invention can be a deoxyribonucleic acid (DNA) molecule or ribonucleic acid (RNA) molecule. Where a polynucleotide is a DNA molecule, that molecule can be a gene or a cDNA molecule. Nucleotide bases are indicated herein by a single letter code: adenine (A), guanine (G), thymine (T), cytosine (C), inosine (1) and uracil (U).

A polynucleotide of the present invention can be prepared using standard techniques well known to one of skill in the art. The preparation of a cDNA molecule encoding a peroxisome proliferator-activated receptor polypeptide of the present invention is described hereinafter in Example 1. A polynucleotide can also be prepared from genomic DNA libraries using lambda phage technologies.

In an alternative aspect, the present invention contemplates an isolated and purified polynucleotide that encodes a peroxisome proliferator-activated receptor polypeptide, said polynucleotide preparable by a process comprising the steps of (a) constructing a library of cDNA clones from a cell that expresses said polypeptide; (b) screening the library with a radio-labelled oligonucleotide probe; (c) identifying a clone that hybridizes to the probe; and (d) isolating the hybridized clone from the library of unhybridized clones. Preferably, the present invention provides an isolated and purified polynucleotide that encodes a peroxisome proliferator-activated receptor polypeptide prepared by a process comprising the steps of (a) constructing a library of cDNA clones from a cell that expresses said polypeptide; (b) screening the library with a radio-labelled oligonucleotide probe; (c) identifying a clone that hybridizes to the probe; and (d) isolating the hybridized clone from the library of unhybridized clones. More preferably, the polypeptide encoded has the amino acid residue sequence of SEQ ID NO: 2. Still more preferably, the polynucleotide comprises the nucleotide sequence of SEQ ID NO: 1.

B. Probes and Primers.

In another aspect, DNA sequence information provided by the present invention allows for the preparation of relatively short DNA (or RNA) sequences having the ability to specifically hybridize to gene sequences of the selected polynucleotides disclosed herein. In these aspects, nucleic acid probes of an appropriate length are prepared based on a consideration of a selected nucleotide sequence, e.g., a sequence such as that shown in SEQ ID NO: 1. The ability of such nucleic acid probes to specifically hybridize to a polynucleotide encoding a peroxisome proliferator-activated receptor lends them particular utility in a variety of embodiments. Most importantly, the probes can be used in a variety of assays for detecting the presence of complementary sequences in a given sample.

In certain embodiments, it is advantageous to use oligonucleotide primers. The sequence of such primers is designed using a polynucleotide of the present invention for use in detecting, amplifying or mutating a defined segment of a gene or polynucleotide that encodes a peroxisome proliferator-activated receptor polypeptide from mammalian cells using polymerase chain reactive (PCR) technology.

To provide certain of the advantages in accordance with the present invention, a preferred nucleic acid sequence employed for hybridization studies or assays includes probe molecules that are complementary to at least a 10 to 70 or so long nucleotide stretch of a polynucleotide that encodes a peroxisome proliferator-activated receptor polypeptide, such as that shown in SEQ ID NO: 1. A size of at least 10 nucleotides in length helps to ensure that the fragment will be of sufficient length to form a duplex molecule that is both stable and selective. Molecules having complementary sequences over stretches greater than 10 bases in length are generally preferred, though, in order to increase stability and selectivity of the hybrid, and thereby improve the quality and degree of specific hybrid molecules obtained. One will generally prefer to design nucleic acid molecules having gene-complementary stretches of 25 to 40 nucleotides, 55 to 70 nucleotides, or even longer where desired. Such fragments can be readily prepared by, for example, directly synthesizing the fragment by chemical means, by application of nucleic acid reproduction technology, such as the PCR technology of U.S. Pat. No. 4,603,102, herein incorporated by reference, or by excising selected DNA fragments from recombinant plasmids containing appropriate inserts and suitable restriction enzyme sites.

Yet another aspect of the present invention contemplates an isolated and purified polynucleotide comprising a base sequence that is identical or complementary to a segment of at least 10 contiguous bases of SEQ ID NO: 1, wherein the polynucleotide hybridizes to a polynucleotide that encodes a peroxisome proliferator-activated receptor polypeptide. Preferably, the isolated and purified polynucleotide comprises a base sequence that is identical or complementary to a segment of at least 25 to 70 contiguous bases of SEQ ID NO: 1. For example, the polynucleotide of the present invention can comprise a segment of nucleotide bases identical or complementary to 40 or 55 contiguous bases of the disclosed nucleotide sequences.

In still another embodiment of the present invention, there is provided an isolated and purified polynucleotide comprising a base sequence that is identical or complementary to a segment of at least 10 contiguous bases of SEQ ID NO: 1. The polynucleotide of the invention hybridizes to SEQ ID NO: 1, or a complement of SEQ ID NO: 1. Preferably, the isolated and purified polynucleotide comprises a base sequence that is identical or complementary to a segment of at least 25 to 70 contiguous bases of SEQ ID NO: 1. For example, the polynucleotide of the invention can comprise a segment of bases identical or complementary to 40 or 55 contiguous bases of SEQ ID NO: 1.

Accordingly, a polynucleotide probe molecule of the invention can be used for its ability to selectively form duplex molecules with complementary stretches of the gene. Depending on the application envisioned, one will desire to employ varying conditions of hybridization to achieve varying degree of selectivity of the probe toward the target sequence. For applications requiring a high degree of selectivity, one will typically desire to employ relatively stringent conditions to form the hybrids. For example, one will select relatively low salt and/or high temperature conditions, such as provided by 0.02 M–0.15 M NaCl at temperatures of 50° C. to 70° C. Those conditions are particularly selective, and tolerate little, if any, mismatch between the probe and the template or target strand.

Of course, for some applications, for example, where one desires to prepare mutants employing a mutant primer strand hybridized to an underlying template or where one seeks to isolate a peroxisome proliferator-activated receptor polypeptide coding sequence from other cells, functional equivalents, or the like, less stringent hybridization conditions are typically needed to allow formation of the heteroduplex. In these circumstances, one can desire to employ conditions such as 0.15 M–0.9 M salt, at temperatures ranging from 20° C. to 55° C. Cross-hybridizing species can thereby be readily identified as positively hybridizing signals with respect to control of hybridizations. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results.

In certain embodiments, it is advantageous to employ a polynucleotide of the present invention in combination with an appropriate label for detecting hybrid formation. A wide variety of appropriate labels are known in the art, including radioactive, enzymatic or other ligands, such as avidin/biotin, which are capable of giving a detectable signal.

In general, it is envisioned that a hybridization probe described herein is useful both as a reagent in solution hybridization as well as in embodiments employing a solid phase. In embodiments involving a solid phase, the test DNA (or RNA) is adsorbed or otherwise affixed to a selected matrix or surface. This fixed nucleic acid is then subjected to specific hybridization with selected probes under desired conditions. The selected conditions depend as is well known in the art on the particular circumstances and criteria required (e.g., on the G+C contents, type of target nucleic acid, source of nucleic acid, size of hybridization probe). Following washing of the matrix to remove nonspecifically bound probe molecules, specific hybridization is detected, or even quantified, by means of the label.

II. Peroxisome Proliferator-activated Receptor Polypeptides

In another embodiment, the present invention contemplates an isolated and purified peroxisome proliferator-activated receptor polypeptide. Preferably, a peroxisome proliferator-activated receptor polypeptide of the invention is a recombinant polypeptide. More preferably, a peroxisome proliferator-activated receptor polypeptide of the present invention is a peroxisome proliferator-activated receptor-γ polypeptide. Even more preferably, a peroxisome proliferator-activated receptor polypeptide of the present invention comprises the amino acid residue sequence of SEQ ID NO:2.

Polypeptides are disclosed herein as amino acid residue sequences. Those sequences are written left to right in the direction from the amino to the carboxy terminus. In accordance with standard nomenclature, amino acid residue sequences are denominated by either a single letter or a three letter code as indicated below.

| Amino Acid Residue | 3-Letter Code | 1-Letter Code |
|---|---|---|
| Alanine | Ala | A |
| Arginine | Arg | R |
| Asparagine | Asn | N |
| Aspartic Acid | Asp | D |
| Cysteine | Cys | C |
| Glutamine | Gln | Q |
| Glutamic Acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

Modifications and changes can be made in the structure of a polypeptide of the present invention and still obtain a molecule having like peroxisome proliferator-activated receptor characteristics. For example, certain amino acids can be substituted for other amino acids in a sequence without appreciable loss of receptor activity. Because it is the interactive capacity and nature of a polypeptide that defines that polypeptide's biological functional activity, certain amino acid sequence substitutions can be made in a polypeptide sequence (or, of course, its underlying DNA coding sequence) and nevertheless obtain a polypeptide with like properties.

In making such changes, the hydropathic index of amino acids can be considered. The importance of the hydropathic amino acid index in conferring interactive biologic function on a polypeptide is generally understood in the art (Kyte & Doolittle, 1982). It is known that certain amino acids can be substituted for other amino acids having a similar hydropathic index or score and still result in a polypeptide with similar biological activity. Each amino acid has been assigned a hydropathic index on the basis of its hydrophobicity and charge characteristics. Those indices are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is believed that the relative hydropathic character of the amino acid determines the secondary structure of the resultant polypeptide, which in turn defines the interaction of the polypeptide with other molecules, such as enzymes, substrates, receptors, antibodies, antigens, and the like. It is known in the art that an amino acid can be substituted by another amino acid having a similar hydropathic index and still obtain a functionally equivalent polypeptide. In such changes, the substitution of amino acids whose hydropathic indices are within ±2 is preferred, those which are within ±1 are particularly preferred, and those within ±0.5 are even more particularly preferred.

Substitution of like amino acids can also be made on the basis of hydrophilicity, particularly where the biological functional equivalent polypeptide or peptide thereby created is intended for use in immunological embodiments. U.S. Pat. No. 4,554,101, incorporated herein by reference, states that the greatest local average hydrophilicity of a polypeptide, as governed by the hydrophilicity of its adjacent amino acids, correlates with its immunogenicity and antigenicity, i.e. with a biological property of the polypeptide.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); proline (−0.5±1); threonine (−0.4); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent polypeptide. In such changes, the substitution of amino acids whose hydrophilicity values are within ±2 is preferred, those which are within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine and isoleucine (see table, below). The present invention thus contemplates functional or biological equivalents of a peroxisome proliferator-activated receptor polypeptide as set forth above.

| Original Residue | Exemplary Substitutions |
| --- | --- |
| Ala | Gly; Ser |
| Arg | Lys |
| Asn | Gln; His |
| Asp | Glu |
| Cys | Ser |
| Gln | Asn |
| Glu | Asp |
| Gly | Ala |
| His | Asn; Gln |
| Ile | Leu; Val |
| Leu | Ile; Val |
| Lys | Arg |
| Met | Met; Leu; Tyr |
| Ser | Thr |
| Thr | Ser |
| Trp | Tyr |
| Tyr | Trp; Phe |
| Val | Ile; Leu |

Biological or functional equivalents of a polypeptide can also be prepared using site-specific mutagenesis. Site-specific mutagenesis is a technique useful in the preparation of second generation polypeptides, or biologically functional equivalent polypeptides or peptides, derived from the sequences thereof, through specific mutagenesis of the underlying DNA. As noted above, such changes can be desirable where amino acid substitutions are desirable. The technique further provides a ready ability to prepare and test sequence variants, for example, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred, with about 5 to 10 residues on both sides of the junction of the sequence being altered.

In general, the technique of site-specific mutagenesis is well known in the art, as exemplified by Adelman, et al., 1983. As will be appreciated, the technique typically employs a phage vector which can exist in both a single stranded and double stranded form. Typical vectors useful in site-directed mutagenesis include vectors such as the M13 phage (Messing et al. 1981). These phage are commercially available and their use is generally known to those of skill in the art.

In general, site-directed mutagenesis in accordance herewith is performed by first obtaining a single-stranded vector which includes within its sequence a DNA sequence which encodes all or a portion of the peroxisome proliferator-activated receptor polypeptide sequence selected. An oligonucleotide primer bearing the desired mutated sequence is prepared, generally synthetically, for example, by the method of Crea, et al., 1978. This primer is then annealed to the singled-stranded vector, and extended by the use of enzymes such as *E. coli* polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells such as *E. coli* cells and clones are selected which include recombinant vectors bearing the mutation. Commercially available kits come with all the reagents necessary, except the oligonucleotide primers.

A polypeptide of the present invention is prepared by standard techniques well known to those skilled in the art. Such techniques include, but are not limited to, isolation and purification from tissues known to contain that polypeptide, and expression from cloned DNA that encodes such a polypeptide using transformed cells (See Example 1, infra.) Analysis of Receptor Functional Regions.

A sizeable amount of information about an orphan receptor is gained from comparisons of the nucleotide sequence and primary structure to those of other steroid hormone receptors, because within the superfamily, functional regions tend to exist as structural modules. The steroid hormone receptor superfamily of transcription factors (Evans, 1988; Short, 1988) are, generally, structurally organized as follows:

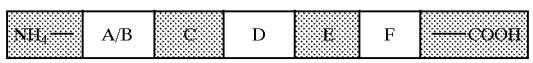

Region C contains two zinc fingers; the first finger and adjacent sequence contains the region that binds to the target DNA and the second finger is apparently involved in dimerization with other steroid hormone receptors. The A and B regions have some transcriptional activating functions, as do regions C, E, and F. A basic region located between C and D, appears to be involved in nuclear localization of the receptor. The E region is the ligand binding domain. Steroid hormone receptors generally bind ligands that are small lipophilic molecules that can pass through cell membranes passively, (e.g. estrogen, progesterone, retinoic acid, or vitamin D.) The E region also is involved in nuclear localization and in binding heat shock protein. Region F, when present, can be involved in transcriptional activation.

Regulation of gene expression in a cell is accomplished through many different mechanisms. A well known mechanism of gene expression regulation is through the use of zinc finger motifs in a polypeptide. The zinc finger motif found in many transcription factors binds to DNA to regulate transcription. Zinc fingers have been identified in many transcription factors including Sp1, estrogen, and glucocorticoid receptors, several Drosophila developmental regulators, and the Xenopus Xf in protein, as well as in the *E. coli* UvrA protein and certain retroviral nucleic acid binding proteins.

Zinc fingers are postulated to bind to the major groove of B-DNA so as to interact with ~5 successive base pairs; that is, with about a half-turn of B-DNA. A zinc finger protein thus can bind to DNA in which the protein binds along one face of the DNA with successive zinc fingers bound in the major groove on alternate sides of the double helix. Zinc fingers likely form structural "scaffolds" that match the double helix's three dimensional contour. Base sequence specificity is presumably provided by the particular sequence of each zinc finger's variable residues (Klug and Rhodes, 1987).

In another embodiment, the polynucleotide that encodes for the zinc finger polypeptide or the zinc finger polypeptide can be used to identify other polynucleotides that encode a zinc finger polypeptide.

There are 3 PPAR genes described in xenopus, PPAR α, β and γ. (Dreyer, 1992). Human PPAR-α has been recently described, although putatively described as a single gene, unlike the xenopus genes, with no closely related family members (Sher, 1993). In the Xenopus system, PPAR α, β and γ show very high amino acid identity in their DNA binding and ligand binding regions, and correspondingly have shown similar abilities to activate the same target DNA sequences, and to be activated by clofibrate and peroxisome proliferator agents (Dreyer, 1992). However, human PPAR α, and now γ, have different chromosomal locations. All species α, β, and γ show differences in A/B and D regions, and all species demonstrate that α, β, and γ have different tissue expression patterns. Amino acid identity between the xenopus γ and human γ receptors, in critical regions, is high enough to expect similar function, and indeed, studies on the human PPAR α by Sher et al. (1993) show it has the same ability as xenopus and murine PPAR α to activate the same reporters. This indicates that the receptor polypeptide of the present invention, human PPAR-γ, is likely to activate these reporters in a manner similar to xenopus PPAR-γ, based on the highly conserved identity in critical regions. However, differences in sequence are significant enough to expect differences in vivo.

The 108–110 aa A/B region [Wahli, 1991 #31] (transactivation domain) is approximately the same size as in the murine PPAR-α (102 aa) (Issemann, 1990) and the xenopus PPAR-γ receptor (112 aa) (Dreyer, 1992) and shows highest identity to the xenopus PPAR-γ receptor (57%). The highly conserved DNA binding C region (DNA binding and dimerization domain) has 97% aa identity with the xenopus PPAR-γ receptor. The D region or linker region (nuclear localization domain), also referred to as the ligand 1 domain (Forman and Samuels, 1990), will generally show the least conservation between nuclear receptor superfamily members binding different ligands, but in subfamilies binding the same ligand there are areas of fairly high identity, and the PPAR family illustrates this concept. As illustrated in FIG. 1, the D region here shows the highest degree of identity (70%) between the PPAR-γs of man and frog. The E region (ligand binding, dimerization, nuclear localization, transactivation domain) of xenopus and human PPAR-γ overall had 75% identity. Closer examination of xenopus and human domains within the E region shows only 7% identity in the first 36 aa after the D region, 90% identity in the 42 aa T1 transactivation silencing subdomain (Forman and Samuels, 1990) and 91% identity in the region extending from the ligand binding and dimerization domains to the carboxyl terminus, (148 aa).

The open reading frame encodes nuclear receptor A/B, C, D, and E regions, and aligns with other members of the family. hPPAR-γ 1 shows 74% amino acid identity in the DNA binding and hinge regions with the murine PPAR α protein, and 90% amino acid identity with the xenopus PPAR γ protein in these same regions, hence the designation as a full length human PPAR-γ.

Of particular note is the conservation of the "CEGCKG-FFRRTIRLK" (SEQ ID NO:8) motif in the C region. This corresponds to the portion of the first cysteine finger of the hPPAR-γ protein that contacts the DNA in PPAR response elements (PPREs) of genes regulated by hPPAR-γ (Kliewer, 1992; O'Malley, 1992; Truss et al., 1993). Conservation of this motif is a strong indicator that this receptor too, will activate the PPREs shown to be regulated by other members of the family, and that it is likely to bind the classic estrogen/retinoid/thyroid receptor half site "AGGTCA" (Truss et al., 1993). Whether it will prefer to bind this half site in direct repeat with another, with one nucleotide spaced between the repeats, referred to as a "DR-1" binding site (Umesono, 1991), as has been shown with murine PPAR-α, is likely. Xenopus PPAR-γ did activate this type of response element (Dreyer et al., 1992). Also of interest is the conservation of the ligand binding domain, region E. Beginning with the highly conserved T1 putative silencing domain, there is very high conservation through the dimerization domain, in particular, of the heptad repeats that have been implicated in heterodimerization (Forman and Samuels, 1990). It should be noted that the points of difference in the D and early E regions may be significant and alter ligand binding.

The shorter transcript observed on northern blot analyses is approximately 0.65 kb, and if the polyadenylation signal was not long, this would encode a predicted protein of approximately 26 kDa. In order for this transcript to encode even a short A/B region, complete C region, short D region and intact E region, it would require at least 1000 base pairs. Thus, the short transcript, if translated, would produce a nuclear receptor that lacks part or all of entire functional regions normally present in members of the superfamily.

Data indicates that the 0.65 kb mRNA was not the result of partial degradation of the RNA. However, mRNA of this size were present on more than one northern blot. Hybridization of these blots with other cDNAs, (c-fos, c-jun, RAR α, and β-actin) showed no evidence for degradation of those mRNAs.

III. Expression Vectors

In an alternative embodiment, the present invention provides an expression vector comprising a polynucleotide that encodes a peroxisome proliferator-activated receptor polypeptide. Preferably, an expression vector of the present invention comprises a polynucleotide that encodes a polypeptide comprising the amino acid residue sequence of SEQ ID NO:2. More preferably, an expression vector of the present invention comprises a polynucleotide comprising the nucleotide base sequence of SEQ ID NO:1. Even more preferably, an expression vector of the invention comprises a polynucleotide operatively linked to an enhancer-promoter. More preferably still, an expression vector of the invention comprises a polynucleotide operatively linked to a prokaryotic promoter. Alternatively, an expression vector of the present invention comprises a polynucleotide operatively linked to an enhancer-promoter that is a eukaryotic promoter, and the expression vector further comprises a polyadenylation signal that is positioned 3' of the carboxy-terminal amino acid and within a transcriptional unit of the encoded polypeptide.

A promoter is a region of a DNA molecule typically within about 100 nucleotide pairs in front of (upstream of) the point at which transcription begins (i.e., a transcription start site). That region typically contains several types of DNA sequence elements that are located in similar relative positions in different genes. As used herein, the term "promoter" includes what is referred to in the art as an upstream promoter region, a promoter region or a promoter of a generalized eukaryotic RNA Polymerase II transcription unit.

Another type of discrete transcription regulatory sequence element is an enhancer. An enhancer provides specificity of time, location and expression level for a particular encoding region (e.g., gene). A major function of an enhancer is to increase the level of transcription of a coding sequence in a cell that contains one or more transcription factors that bind to that enhancer. Unlike a promoter, an enhancer can function when located at variable distances from transcription start sites so long as a promoter is present.

As used herein, the phrase "enhancer-promoter" means a composite unit that contains both enhancer and promoter elements. An enhancer-promoter is operatively linked to a coding sequence that encodes at least one gene product. As used herein, the phrase "operatively linked" means that an enhancer-promoter is connected to a coding sequence in such a way that the transcription of that coding sequence is controlled and regulated by that enhancer-promoter. Means for operatively linking an enhancer-promoter to a coding sequence are well known in the art. As is also well known in the art, the precise orientation and location relative to a coding sequence whose transcription is controlled, is dependent inter alia upon the specific nature of the enhancer-promoter. Thus, a TATA (SEQ ID NO:9) box minimal promoter is typically located from about 25 to about 30 base pairs upstream of a transcription initiation site and an upstream promoter element is typically located from about 100 to about 200 base pairs upstream of a transcription initiation site. In contrast, an enhancer can be located downstream from the initiation site and can be at a considerable distance from that site.

An enhancer-promoter used in a vector construct of the present invention can be any enhancer-promoter that drives expression in a cell to be transfected. By employing an enhancer-promoter with well-known properties, the level and pattern of gene product expression can be optimized.

A coding sequence of an expression vector is operatively linked to a transcription terminating region. RNA polymerase transcribes an encoding DNA sequence through a site where polyadenylation occurs. Typically, DNA sequences located a few hundred base pairs downstream of the polyadenylation site serve to terminate transcription. Those DNA sequences are referred to herein as transcription-termination regions. Those regions are required for efficient polyadenylation of transcribed messenger RNA (mRNA). Transcription-terminating regions are well known in the art. A preferred transcription-terminating region used in an adenovirus vector construct of the present invention comprises a polyadenylation signal of SV40 or the protamine gene.

An expression vector comprises a polynucleotide that encodes a peroxisome proliferator-activated receptor polypeptide. Such a polypeptide is meant to include a sequence of nucleotide bases encoding a peroxisome proliferator-activated receptor polypeptide sufficient in length to distinguish said segment from a polynucleotide segment encoding a non-peroxisome proliferator-activated receptor polypeptide. A polypeptide of the invention can also encode biologically functional polypeptides or peptides which have variant amino acid sequences, such as with changes selected based on considerations such as the relative hydropathic score of the amino acids being exchanged. These variant sequences are those isolated from natural sources or induced in the sequences disclosed herein using a mutagenic procedure such as site-directed mutagenesis.

Preferably, the expression vectors of the present invention comprise polynucleotide that encode polypeptides comprising the amino acid residue sequence of SEQ ID NO: 2. An expression vector can include a peroxisome proliferator-activated receptor polypeptide coding region itself of any of the peroxisome proliferator-activated receptor polypeptides noted above or it can contain coding regions bearing selected alterations or modifications in the basic coding region of such a peroxisome proliferator-activated receptor polypeptide. Alternatively, such vectors or fragments can code larger polypeptides or polypeptides which nevertheless include the basic coding region. In any event, it should be appreciated that due to codon redundancy as well as biological functional equivalence, this aspect of the invention is not limited to the particular DNA molecules corresponding to the polypeptide sequences noted above.

Exemplary vectors include the mammalian expression vectors of the pCMV family including pCMV6b and pCMV6c (Chiron Corp., Emeryville Calif.). In certain cases, and specifically in the case of these individual mammalian expression vectors, the resulting constructs can require co-transfection with a vector containing a selectable marker such as pSV2neo. Via co-transfection into a dihydrofolate reductase-deficient Chinese hamster ovary cell line, such as DG44, clones expressing peroxisome proliferator-activated receptor polypeptides by virtue of DNA incorporated into such expression vectors can be detected.

A DNA molecule of the present invention can be incorporated into a vector by a number of techniques which are well known in the art. For instance, the vector pUC18 has been demonstrated to be of particular value. Likewise, the related vectors M13mp18 and M13mp19 can be used in certain embodiments of the invention, in particular, in performing dideoxy sequencing.

An expression vector of the present invention is useful both as a means for preparing quantities of the peroxisome proliferator-activated receptor polypeptide-encoding DNA itself, and as a means for preparing the encoded polypeptide and peptides. It is contemplated that where peroxisome proliferator-activated receptor polypeptides of the invention are made by recombinant means, one can employ either prokaryotic or eukaryotic expression vectors as shuttle systems. However, in that prokaryotic systems are usually incapable of correctly processing precursor polypeptides and, in particular, such systems are incapable of correctly processing membrane associated eukaryotic polypeptides, and since eukaryotic peroxisome proliferator-activated receptor polypeptides are anticipated using the teaching of the disclosed invention, one likely expresses such sequences in eukaryotic hosts. However, even where the DNA segment encodes a eukaryotic peroxisome proliferator-activated receptor polypeptide, it is contemplated that prokaryotic expression can have some additional applicability. Therefore, the invention can be used in combination with vectors which can shuttle between the eukaryotic and prokaryotic cells. Such a system is described herein which allows the use of bacterial host cells as well as eukaryotic host cells.

Where expression of recombinant peroxisome proliferator-activated receptor polypeptides is desired and a eukaryotic host is contemplated, it is most desirable to employ a vector such as a plasmid, that incorporates a eukaryotic origin of replication. Additionally, for the purposes of expression in eukaryotic systems, one desires to position the peroxisome proliferator-activated receptor encoding sequence adjacent to and under the control of an effective eukaryotic promoter such as promoters used in combination with Chinese hamster ovary cells. To bring a coding sequence under control of a promoter, whether it is eukaryotic or prokaryotic, what is generally needed is to position the 5' end of the translation initiation side of the proper translational reading frame of the polypeptide between about 1 and about 50 nucleotides 3' of or downstream with respect to the promoter chosen. Furthermore, where eukaryotic expression is anticipated, one would typically desire to incorporate into the transcriptional unit which includes the peroxisome proliferator-activated receptor polypeptide, an appropriate polyadenylation site.

Incorporation of polynucleotides of the present invention into expression vectors can be achieved by a variety of techniques that will be recognized by those of ordinary skill in the art. For example, excised inserts of the hPPAR-γ transcripts of the present invention can be blunt ended and ligated into blunt ended pcINEO (Introvigen) plasmids which contain the constitutively active CMV promoter, a multiple cloning site cassette flanked by T7 and SP6 promoters to ascertain directionality, as well as a NEO cassette to allow for neomycin selection. Hela cell lines stably expressing the hPPAR-γ polypeptides can be created by subcloning cDNA inserts into the pMV 7 and pMV 12 retroviral expression vectors. These vectors have been proven to be capable of generation of stable mammalian cell lines in the following manner: pMV 7 and pMV 12 plasmids, each containing a hPPAR-γ cDNA, are transfected by lipofection technique into Ψ2 cells. Selection for cells expressing the virus-encoded gene is done after 48 hours with G418 (for pMV 7 transfections) or hygromycin B (for pMV 12 transfections). After one week of selection, surviving cells are pooled and used to produce ecotropic retrovirus, which is then used to infect the amphotropic producer cell line PA317, which will generate higher titer virus that can infect all mammalian cells. Selected PA317 cells can be used to produce virus, which in turn is used to infect Hela cells. After selection, resistant Hela cell clones are selected and expanded as clonal cell lines. Presence of hPPAR-γ transcripts and polypeptides can he confirmed through western and northern blot analysis.

The pCMV plasmids are a series of mammalian expression vectors of particular utility in the present invention. The vectors are designed for use in essentially all cultured cells and work extremely well in SV40-transformed simian COS cell lines. The pCMV1, 2, 3, and 5 vectors differ from each other in certain unique restriction sites in the polylinker region of each plasmid. The pCMV4 vector differs from these 4 plasmids in containing a translation enhancer in the sequence prior to the polylinker. While they are not directly derived from the pCMV 1–5 series of vectors, the functionally similar pCMV6b and c vectors are available from the Chiron Corp. of Emeryville, Calif. and are identical except for the orientation of the polylinker region which is reversed in one relative to the other.

The universal components of the pCMV plasmids are as follows. The vector backbone is pTZ18R (Pharmacia), and contains a bacteriophage f1 origin of replication for production of single stranded DNA and an ampicillin-resistance gene. The CMV region consists of nucleotides −760 to +3 of the powerful promoter-regulatory region of the human cytomegalovirus (Towne stain) major immediate early gene (Thomsen et al., 1984; Boshart et al., 1985). The human growth hormone fragment (hGH) contains transcription termination and poly-adenylation signals representing sequences 1533 to 2157 of this gene (Seeburg, 1982). There is an Alu middle repetitive DNA sequence in this fragment. Finally, the SV40 origin of replication and early region promoter-enhancer derived from the pcD-X plasmid (HindII to PstI fragment) described in (Okayama et al., 1983). The promoter in this fragment is oriented such that transcription proceeds away from the CMV/hGH expression cassette.

The pCMV plasmids are distinguishable from each other by differences in the polylinker region and by the presence or absence of the translation enhancer. The starting pCMV1 plasmid has been progressively modified to render an increasing number of unique restriction sites in the polylinker region. To create pCMV2, one of two EcoRI sites in pCMV1 were destroyed. To create pCMV3, pCMV1 was modified by deleting a short segment from the SV40 region (StuI to EcoRI), and in so doing made unique the PstI, SalI, and BamHI sites in the polylinker. To create pCMV4, a synthetic fragment of DNA corresponding to the 5'-untranslated region of a mRNA transcribed from the CMV promoter was added C. The sequence acts as a translational enhancer by decreasing the requirements for initiation factors in polypeptide synthesis. To create pCMV5, a segment of DNA (HpaI to EcoRI) was deleted from the SV40 origin region of pCMV1 to render unique all sites in the starting polylinker.

The pCMV vectors have been successfully expressed in simian COS cells, mouse L cells, CHO cells, and HeLa cells. In several side by side comparisons they have yielded 5- to 10-fold higher expression levels in COS cells than SV40-based vectors. The pCMV vectors have been used to express the LDL receptor, nuclear factor 1, G, alpha polypeptide, polypeptide phosphatase, synaptophysin, synapsin, insulin receptor, influenza hemagglutinin, androgen receptor, sterol 26-hydroxylase, steroid 17- and 21-hydroxylase, cytochrome P-450 oxidoreductase, beta-adrenergic receptor, folate receptor, cholesterol side chain cleavage enzyme, and a host of other cDNAs. It should be noted that the SV40 promoter in these plasmids can be used to express other genes such as dominant selectable markers. Finally, there is an ATG sequence in the polylinker between the HindIII and PstI sites in pCMU that can cause spurious translation initiation. This codon should be avoided if possible in expression plasmids. A paper describing the construction and use of the parenteral pCMV1 and pCMV4 vectors has been published.

IV. Transfected Cells

In yet another embodiment, the present invention provides a recombinant host cell transfected with a polynucleotide that encodes a peroxisome proliferator-activated receptor polypeptide. Preferably, a recombinant host cell of the present invention is transfected with the polynucleotide of SEQ ID NO:1. Even more preferably, a host cell of the invention is a eukaryotic host cell. Still more preferably, a recombinant host cell of the present invention is a yeast cell. Alternatively, a recombinant host cell of the invention can be, by way of example and withoiut limitation, a COS-1 cell, or a HeLa cell or a CV-1 cell. Means of transforming or transfecting cells with exogenous polynucleotide such as DNA molecules are well known in the art and include techniques such as calcium-phosphate- or DEAE-dextran-mediated transfection, protoplast fusion, electroporation, liposome mediated transfection, direct microinjection and adenovirus infection (Sambrook et al., 1989).

*Saccharomyces cerevisiase* or common baker's yeast is the most commonly used among eukaryotic microorganisms, although a number of other strains are commonly available. For expression in Saccharomyces, the plasmid YRp7, for example, is commonly used (Stinchcomb et al., 1979; Kingsman et al., 1979; Tschemper et al., 1980). This plasmid already contains the trp1 gene which provides a selection marker for a mutant strain of yeast lacking the ability to grow in tryptophan, for example ATCC No. 44076 or PEP4-1 (Jones, 1977). The presence of the trpl lesion as a characteristic of the yeast host cell genome then provides an effective environment for detecting transformation by growth in the absence of tryptophan.

Suitable promoter sequences in yeast vectors include the promoters for 3-phosphoglycerate kinase (Hitzeman et al., 1980) or other glycolytic enzymes (Hess et al., 1968; Holland et al., 1978) such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also introduced into the expression vector downstream from the sequences to be expressed to provide polyadenylation of the mRNA and termination. Other promoters, which have the additional advantage of transcription controlled by growth conditions are the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization. Any plasmid vector containing a yeast-compatible promoter, origin or replication and termination sequences is suitable.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, *E. coli* can be transformed using pBR322, a plasmid derived from an *E. coli* species (Bolivar et al., 1977). pBR322 contains genes for ampicillin and tetracycline resistance and thus provides easy means for identifying transformed cells. The pBR plasmid, or other microbial plasmid or phage must also contain, or be modified to contain, promoters which can be used by the microbial organism for expression of its own polypeptides.

Those promoters most commonly used in recombinant DNA construction include the β-lactamase (penicillinase) and lactose promoter systems (Chang et al., 1978; Itakura et al., 1977; Goeddel et al., 1979; Goeddel et al., 1980) and a tryptophan (TRP) promoter system (EPO Appl. Publ. No. 0036776; Siebwenlist et al., 1980). While these are the most commonly used, other microbial promoters have been discovered and utilized, and details concerning their nucleotide sequences have been published, enabling a skilled worker to introduce functional promoters into plasmid vectors (Siebwenlist et al., 1980).

In another aspect, a recombinant host cell of the present invention is a prokaryotic host cell. Preferably, a recombinant host cell of the invention is a bacterial cell of the DH5α strain of *Escherichia coli*. More preferably, a recombinant host cell comprises a polynucleotide under the transcriptional control of regulatory signals functional in the recombinant host cell, wherein the regulatory signals appropriately control expression of a peroxisome proliferator-activated receptor polypeptide in a manner to enable all necessary transcriptional and post-transcriptional modification. The aforementioned strains, as well as *E. coil* W3110 (F-, lambda-, prototrophic, ATCC No. 273325), bacilli such as *Bacillus subrilus*, or other enterobacteriaceae such as *Salmonella ryphimurium* or *Serratus marcesans*, and various Pseudomonas species can be used.

The most widely used method is transfection mediated by either calcium phosphate or DEAE-dextran. Although the mechanism remains obscure, it is believed that the transfected DNA enters the cytoplasm of the cell by endocytosis and is transported to the nucleus. Depending on the cell type, up to 90% of a population of cultured cells can be transfected at any one time. Because of its high efficiency, transfection mediated by calcium phosphate or DEAE-dextran is the method of choice for experiments that require transient expression of the foreign DNA in large numbers of cells. Calcium phosphate-mediated transfection is also used to establish cell lines that integrate copies of the foreign DNA, which are usually arranged in head-to-tail tandem arrays into the host cell genome.

In the protoplast fusion method, protoplasts derived from bacteria carrying high numbers of copies of a plasmid of interest are mixed directly with cultured mammalian cells. After fusion of the cell membranes (usually with polyethylene glycol), the contents of the bacteria are delivered into the cytoplasm of the mammalian cells and the plasmid DNA is transported to the nucleus. Protoplast fusion is not as efficient as transfection for many of the cell lines that are commonly used for transient expression assays, but it is useful for cell lines in which endocytosis of DNA occurs inefficiently. Protoplast fusion frequently yields multiple copies of the plasmid DNA tandemly integrated into the host chromosome.

The application of brief, high-voltage electric pulses to a variety of mammalian and plant cells leads to the formation of nanometer-sized pores in the plasma membrane. DNA is taken directly into the cell cytoplasm either through these pores or as a consequence of the redistribution of membrane components that accompanies closure of the pores. Electroporation can be extremely efficient and can be used both for transient expression of cloned genes and for establishment of cell lines that carry integrated copies of the gene of interest. Electroporation, in contrast to calcium phosphate-mediated transfection and protoplast fusion, frequently gives rise to cell lines that carry one, or at most a few, integrated copies of the foreign DNA.

Liposome transfection involves encapsulation of DNA and RNA within liposomes, followed by fusion of the liposomes with the cell membrane. The mechanism of how DNA is delivered into the cell is unclear but transfection efficiencies can be as high as 90%.

Direct microinjection of a DNA molecule into nuclei has the advantage of not exposing DNA to cellular components such as low-pH endosomes. Microinjection is therefore used primarily as a method to establish lines of cells that carry integrated copies of the DNA of interest.

The use of adenovirus as a vector for cell transfection is well known in the art. Adenovirus vector-mediated cell transfection has been reported for various cells (Stratford-Perricaudet et al., 1992).

In addition to microorganisms, cultures of cells derived from multicellular organisms can also be used as hosts. In principle, any such cell culture is workable, whether from vertebrate or invertebrate culture. However, interest has been greatest in vertebrate cells, and propagation of vertebrate cells in culture (tissue culture) has become a routine procedure in recent years (Kruse and Peterson, 1973). Examples of such useful host cell lines are AtT-20, VERO and HeLa cells, Chinese hamster ovary (CHO) cell lines, and W138, BHK, COSM6, COS-7, 293 and MDCK cell lines. Expression vectors for such cells ordinarily include (if necessary) an origin of replication, a promoter located upstream of the gene to be expressed, along with any necessary ribosome binding sites, RNA splice sites, polyadenylation site, and transcriptional terminator sequences.

For use in mammalian cells, the control functions on the expression vectors are often derived from viral material. For example, commonly used promoters are derived from polyoma, Adenovirus 2, Cytomegalovirus and most frequently Simian Virus 40 (SV40). The early and late promoters of SV40 virus are particularly useful because both are obtained easily from the virus as a fragment which also contains the SV40 viral origin of replication (Fiers et al., 1978). Smaller or larger SV40 fragments can also be used, provided there is included the approximately 250 bp sequence extending from the HindIII site toward the BglI site located in the viral origin of replication. Further, it is also possible, and often desirable, to utilize promoter or control sequences normally associated with the desired gene sequence, provided such control sequences are compatible with the host cell systems.

An origin of replication can be provided with by construction of the vector to include an exogenous origin, such as can be derived from SV40 or other viral (e.g., Polyoma, Adeno, VSV, BPV, CMV) source, or can be provided by the host cell chromosomal replication mechanism. If the vector is integrated into the host cell chromosome, the latter is often sufficient.

V. Preparing Recombinant Peroxisome Proliferator-Activated Receptor Polypeptides In yet another embodiment, the present invention contemplates a process of preparing a peroxisome proliferator-activated receptor polypeptide comprising transfecting a cell with a polynucleotide that encodes a peroxisome proliferator-activated receptor polypeptide to produce a transformed host cell; and maintaining the transformed host cell under biological conditions sufficient for expression of the polypeptide. Preferably, the transformed host cell is a eukaryotic cell. More preferably still, the eukaryotic cell is a COS-1 cell. Alternatively, the host cell is a prokaryotic cell. More preferably, the prokaryotic cell is a bacterial cell of the DH5α strain of $Escherichia$ $coli$. Even more preferably, a polynucleotide transfected into the transformed cell comprises the nucleotide base sequence of SEQ ID NO:1.

A host cell used in the process is capable of expressing a functional, recombinant peroxisome proliferator-activated receptor polypeptide. A preferred host cell is a Chinese hamster ovary cell. However, a variety of cells are amenable to a process of the invention, for instance, yeasts cells, human cell lines, and other eukaryotic cell lines known well to those of skill in the art.

Following transfection, the cell is maintained under culture conditions for a period of time sufficient for expression of a peroxisome proliferator-activated receptor polypeptide. Culture conditions are well known in the art and include ionic composition and concentration, temperature, pH and the like. Typically, transfected cells are maintained under culture conditions in a culture medium. Suitable medium for various cell types are well known in the art. In a preferred embodiment, temperature is from about 20° C. to about 50° C., more preferably from about 30° C. to about 40° C. and, even more preferably about 37° C.

pH is preferably from about a value of 6.0 to a value of about 8.0, more preferably from about a value of about 6.8 to a value of about 7.8 and, most preferably about 7.4. Osmolality is preferably from about 200 milliosmols per liter (mosm/L) to about 400 mosm/l and, more preferably from about 290 mosm/L to about 310 mosm/L. Other biological conditions needed for transfection and expression of an encoded protein are well known in the art.

Transfected cells are maintained for a period of time sufficient for expression of a peroxisome proliferator-activated receptor polypeptide. A suitable time depends inter alia upon the cell type used and is readily determinable by a skilled artisan. Typically, maintenance time is from about 2 to about 14 days.

Recombinant peroxisome proliferator-activated receptor polypeptide is recovered or collected either from the transfected cells or the medium in which those cells are cultured. Recovery comprises isolating and purifying the peroxisome proliferator-activated receptor polypeptide. Isolation and purification techniques for polypeptides are well known in the art and include such procedures as precipitation, filtration, chromatography, electrophoresis and the like.

VI. Antibodies and Methods

In still another embodiment, the present invention provides an antibody immunoreactive with a peroxisome proliferator-activated receptor polypeptide. Preferably, an antibody of the invention is a monoclonal antibody. More preferably, the antibody is immunoreactive with a peroxisome proliferator-activated receptor polypeptide that comprises the amino acid residue sequence of SEQ ID NO:2. Means for preparing and characterizing antibodies are well known in the art (See, e.g., *Antibodies "A Laboratory Manual,"* E. Howell and D. Lane, Cold Spring Harbor Laboratory, 1988).

Briefly, a polyclonal antibody is prepared by immunizing an animal with an immunogen comprising a polypeptide or polynucleotide of the present invention, and collecting antisera from that immunized animal. A wide range of animal species can be used for the production of antisera. Typically an animal used for production of anti-antisera is a rabbit, a mouse, a rat, a hamster or a guinea pig. Because of the relatively large blood volume of rabbits, a rabbit is a preferred choice for production of polyclonal antibodies.

As is well known in the art, a given polypeptide or polynucleotide may vary in its immunogenicity. It is often necessary therefore to couple the immunogen (e.g., a polypeptide or polynucleotide) of the present invention with a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers.

Means for conjugating a polypeptide or a polynucleotide to a carrier protein are well known in the art and include glutaraldehyde, m-maleimidobencoyl-N-hydroxysucciniinide ester, carbodiimide and bis-biazotized benzidine.

As is also well known in the art, immunogencity to a particular immunogen can be enhanced by the use of non-specific stimulators of the immune response known as adjuvants. Exemplary and preferred adjuvants include complete Freund's adjuvant, incomplete Freund's adjuvants and aluminum hydroxide adjuvant.

The amount of immunogen used of the production of polyclonal antibodies varies inter alia, upon the nature of the immunogen as well as the animal used for immunization. A variety of routes can be used to administer the immunogen (subcutaneous, intramuscular, intradermal, intravenous and intraperitoneal. The production of polyclonal antibodies is monitored by sampling blood of the immunized animal at various points following immunization. When a desired level of immunogenicity is obtained, the immunized animal can be bled and the serum isolated and stored.

In another aspect, the present invention contemplates a process of producing an antibody immunoreactive with a peroxisome proliferator-activated receptor polypeptide comprising the steps of (a) transfecting a recombinant host cell with a polynucleotide that encodes a peroxisome proliferator-activated receptor polypeptide; (b) culturing the host cell under conditions sufficient for expression of the polypeptide; (c) recovering the polypeptide; and (d) preparing the antibody to the polypeptide. Preferably, the host cell is transfected with the polynucleotide of SEQ ID NO:1. Even more preferably, the present invention provides an antibody prepared according to the process described above.

A monoclonal antibody of the present invention can be readily prepared through use of well-known techniques such as those exemplified in U.S. Pat. No. 4,196,265, herein incorporated by reference. Typically, a technique involves first immunizing a suitable animal with a selected antigen (e.g., a polypeptide or polynucleotide of the present invention) in a manner sufficient to provide an immune response. Rodents such as mice and rats are preferred animals. Spleen cells from the immunized animal are then fused with cells of an immortal myeloma cell. Where the immunized animal is a mouse, a preferred myeloma cell is a murine NS-1 myeloma cell.

The fused spleen/myeloma cells are cultured in a selective medium to select fused spleen/myeloma cells from the parental cells. Fused cells are separated from the mixture of non-fused parental cells, for example, by the addition of agents that block the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides. Where azaserine is used, the media is supplemented with hypoxanthine.

This culturing provides a population of hybridomas from which specific hybridomas are selected. Typically, selection of hybridomas is performed by culturing the cells by single-clone dilution in microtiter plates, followed by testing the individual clonal supernatants for reactivity with an antigen-polypeptide. The selected clones can then be propagated indefinitely to provide the monoclonal antibody.

By way of specific example, to produce an antibody of the present invention, mice are injected intraperitoneally with between about 1–200 μg of an antigen comprising a polypeptide of the present invention. B lymphocyte cells are stimulated to grow by injecting the antigen in association with an adjuvant such as complete Freund's adjuvant (a non-specific stimulator of the immune response containing killed *Mycobacterium tuberculosis*). At some time (e.g., at least two weeks) after the first injection, mice are boosted by injection with a second dose of the antigen mixed with incomplete Freund's adjuvant.

A few weeks after the second injection, mice are tail bled and the sera titered by immunoprecipitation against radio-labeled antigen. Preferably, the process of boosting and titering is repeated until a suitable titer is achieved. The spleen of the mouse with the highest titer is removed and the spleen lymphocytes are obtained by homogenizing the spleen with a syringe. Typically, a spleen from an immunized mouse contains approximately $5 \times 10^7$ to $2 \times 10^8$ lymphocytes.

Mutant lymphocyte cells known as myeloma cells are obtained from laboratory animals in which such cells have been induced to grow by a variety of well-known methods. Mycloma cells lack the salvage pathway of nucleotide biosynthesis. Because myeloma cells are tumor cells, they can be propagated indefinitely in tissue culture, and are thus denominated immortal. Numerous cultured cell lines of myeloma cells from mice and rats, such as murine NS-1 myeloma cells, have been established.

Myeloma cells are combined under conditions appropriate to foster fusion with the normal antibody-producing cells from the spleen of the mouse or rat injected with the antigen/polypeptide of the present invention. Fusion conditions include, for example, the presence of polyethylene glycol. The resulting fused cells are hybridoma cells. Like myeloma cells, hybridoma cells grow indefinitely in culture.

Hybridoma cells are separated from unfused myeloma cells by culturing in a selection medium such as HAT media (hypoxanthine, aminopterin, thymidine). Unfused myeloma cells lack the enzymes necessary to synthesize nucleotides from the salvage pathway because they are killed in the presence of aminopterin, methotrexate, or azaserine. Unfused lymphocytes also do not continue to grow in tissue culture. Thus, only cells that have successfully fused (hybridoma cells) can grow in the selection media.

Each of the surviving hybridoma cells produces a single type of antibody. These cells are then screened for the production of the specific antibody immunoreactive with an antigen/polypeptide of the present invention. Single cell hybridomas are isolated by limiting dilutions of the hybridomas. The hybridomas are serially diluted many times and, after the dilutions are allowed to grow, the supernatant is tested for the presence of the monoclonal antibody. The clones producing that antibody are then cultured in large amounts to produce an antibody of the present invention in convenient quantity.

VII. Detecting Polynucleotides and the Polypeptides Encoded

By use of a monoclonal antibody of the present invention, specific polypeptides and polynucleotide of the invention can be recognized as antigens, and thus identified. Once identified, those polypeptides and polynucleotide can be isolated and purified by techniques such as antibody-affinity chromatography. In antibody-affinity chromatography, a monoclonal antibody is bound to a solid substrate and exposed to a solution containing the desired antigen. The antigen is removed from the solution through an immunospecific reaction with the bound antibody. The polypeptide or polynucleotide is then easily removed from the substrate and purified.

The present invention thus provides a process of detecting a peroxisome proliferator-activated receptor polypeptide, wherein the process comprises immunoreacting the polypeptide with an antibody prepared according to the process described above to form an antibody-polypeptide conjugate, and detecting the conjugate.

In yet another embodiment, the present invention contemplates a process of detecting a messenger RNA transcript that encodes a peroxisome proliferator-activated receptor polypeptide, wherein the process comprises (a) hybridizing the messenger RNA transcript with a polynucleotide sequence that encodes the peroxisome proliferator-activated receptor polypeptide to form a duplex; and (b) detecting the duplex. Alternatively, the present invention provides a process of detecting a DNA molecule that encodes a peroxisome proliferator-activated receptor polypeptide, wherein the process comprises (a) hybridizing DNA molecules with a polynucleotide that encodes a peroxisome proliferator-activated receptor polypeptide to form a duplex; and (b) detecting the duplex.

VIII. Pharmaceutical Compositions

Alternatively, the present invention contemplates a pharmaceutical composition comprising a peroxisome proliferator-activated receptor polypeptide and a physiologically acceptable carrier. Preferably, the present invention provides a pharmaceutical composition comprising a receptor polypeptide that comprises the amino acid residue sequence of SEQ ID NO:2. In another embodiment, the present invention provides a pharmaceutical composition comprising a polynucleotide that encodes a peroxisome proliferator-activated receptor polypeptide, and a physiologically acceptable carrier. Preferably, that pharmaceutical composition comprises a polynucleotide encoding a receptor polypeptide comprising the amino acid residue sequence of SEQ ID NO:2. Even more preferably, the pharmaceutical composition comprises a polynucleotide that comprises the nucleotide sequence of SEQ ID NO:1.

A composition of the present invention is typically administered parenterally in dosage unit formulations containing standard, well-known nontoxic physiologically acceptable carriers, adjuvants, and vehicles as desired. The term parenteral as used herein includes intravenous, intramuscular, intraarterial injection, or infusion techniques.

Injectable preparations, for example sterile injectable aqueous or oleaginous suspensions, are formulated according to the known art using suitable dispersing or wetting agents and suspending agents. The sterile injectable preparation can also be a sterile injectable solution or suspension in a nontoxic parenterally acceptable diluent or solvent, for example, as a solution in 1,3-butanediol.

Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil can be employed including synthetic mono- or di-glycerides. In addition, fatty acids such as oleic acid find use in the preparation of injectables.

Preferred carriers include neutral saline solutions buffered with phosphate, lactate, Tris, and the like. Of course, one purifies the vector sufficiently to render it essentially free of undesirable contaminants, such as defective interfering adenovirus particles or endotoxins and other pyrogens such that it does not cause any untoward reactions in the individual receiving the vector construct. A preferred means of purifying the vector involves the use of buoyant density gradients, such as cesium chloride gradient centrifugation.

A carrier can also be a liposome. Means for using liposomes as delivery vehicles are well known in the art (See, e.g. Gabizon et al., 1990; Ferruti et al., 1986; and Ranade, 1989).

A transfected cell can also serve as a carrier. By way of example, a liver cell can be removed from an organism, transfected with a polynucleotide of the present invention using methods set forth above and then the transfected cell returned to the organism (e.g. injected intravascularly).

IX. Screening Assays

In yet another aspect, the present invention contemplates a process of screening substances for their ability to interact with a peroxisome proliferator-activated receptor polypeptide comprising the steps of providing a peroxisome proliferator-activated receptor polypeptide, and testing the ability of selected substances to interact with the peroxisome proliferator-activated receptor polypeptide. In a preferred embodiment, providing a peroxisome proliferator-activated receptor polypeptide is transfecting a host cell with a polynucleotide that encodes a peroxisome proliferator-activated receptor polypeptide to form a transformed cell and maintaining the transformed cell under biological conditions sufficient for expression of the peroxisome proliferator-activated receptor polypeptide.

Utilizing the methods and compositions of the present invention, screening assays for the testing of candidate substances such as agonists and antagonists of peroxisome proliferator-activated receptors can be derived. A candidate substance is a substance which potentially can interact with or modulate, by binding or other intramolecular interaction, a peroxisome proliferator-activated receptor polypeptide. In some instances, such a candidate substance will be an agonist of the receptor and in other instances can exhibit antagonistic attributes when interacting with the receptor polypeptide. In other instances, such substances can have mixed agonistic and antagonistic properties or can modulate the peroxisome proliferator-activated receptor in other ways.

Cloned expression systems such as those of the present invention are useful where there is difficulty in obtaining tissue that satisfactorily expresses a particular receptor. Cost is another very real advantage, at least with regard to the microbial expression systems of the present invention. For antagonists in a primary screen, microorganism expression systems of the present invention are inexpensive in comparison to prior art tissue-screening methods.

With the availability of cloned receptors, recombinant receptor screening systems have several advantages over tissue based systems. A major advantage is that the investigator can now control the type of receptor that is utilized in a screening assay. Specific receptor sub-types and sub-sub-types can be preferentially expressed and its interaction with a ligand can be identified. Other advantages include the availability of large amounts of receptor, the availability of rare receptors previously unavailable in tissue samples, and the lack of expenses associated with the maintenance of live animals.

Screening assays of the present invention generally involve determining the ability of a candidate substance to bind to the receptor and to affect the activity of the receptor, such as the screening of candidate substances to identify those that inhibit or otherwise modify the receptor's function. Typically, this method includes preparing recombinant receptor polypeptide, followed by testing the recombinant polypeptide or cells expressing the polypeptide with a candidate substance to determine the ability of the substance to affect its physiological function. In preferred embodiments, the invention relates to the screening of candidate substances to identify those that affect the transcription regulation activity of the human receptor, and thus can be suitable for use in humans.

As is well known in the art, a screening assay provides a receptor under conditions suitable for the binding of an agent to the receptor. These conditions include but are not limited to pH, temperature, tonicity, the presence of relevant co-factors, and relevant modifications to the polypeptide such as glycosylation or prenylation. It is contemplated that the receptor can be expressed and utilized in a prokaryotic or eukaryotic cell. The host cell expressing the receptor can be used whole or the receptor can be isolated from the host cell. The host cell can also be fractionated into sub-cellular fractions where the receptor can be found. For example, cells expressing the receptor can be fractionated into the nuclei, the endoplasmic reticulum, vesicles, or the membrane surfaces of the cell.

pH is preferably from about a value of 6.0 to a value of about 8.0, more preferably from about a value of about 6.8 to a value of about 7.8 and, most preferably about 7.4. In a preferred embodiment, temperature is from about 20° C. to about 50° C., more preferably from about 30° C. to about 40° C. and, even more preferably about 37° C. Osmolality is preferably from about 5 milliosmols per liter (mosm/L) to about 400 mosm/l and, more preferably from about 200 milliosmols per liter to about 400 mosm/l and, even more preferably from about 290 mosm/L to about 310 mosm/L. The presence of co-factors can be required for the proper functioning of the receptor. Typical co-factors include sodium, potassium, calcium, magnesium, and chloride. In addition, small, non-peptide molecules, known as prosthetic groups can be required. Other biological conditions needed for receptor function are well known in the art.

It is well known in the art that proteins can be reconstituted in artificial membranes, vesicles or liposomes (Danboldt et al., 1990). The present invention contemplates that the receptor can be incorporated into artificial membranes, vesicles or liposomes. The reconstituted receptor can be utilized in screening assays.

It is further contemplated that the receptor of the present invention can be coupled to a solid support. The solid support can be agarose beads, polyacrylainide beads, polyacrylic beads or other solid matrices capable of being coupled to proteins. Well known coupling agents include cyanogen bromide, carbonyldiimidazole, tosyl chloride, and gluteraldehyde.

It is further contemplated that secondary polypeptides which can function in conjunction with the receptor of the present invention can be provided. For example, the receptor of the present invention exerts its physiological effects in conjunction with a G-protein and an effector polypeptide.

In a typical screening assay for identifying candidate substances, one employs the same recombinant expression host as the starting source for obtaining the receptor polypeptide, generally prepared in the form of a crude homogenate. Recombinant cells expressing the receptor are washed and homogenized to prepare a crude polypeptide homogenate in a desirable buffer such as disclosed herein. In a typical assay, an amount of polypeptide from the cell homogenate, is placed into a small volume of an appropriate assay buffer at an appropriate pH. Candidate substancesare added to the admixture in convenient concentrations and the interaction between the candidate substance and the receptor polypeptide is monitored.

Where one uses an appropriate known substrate for the receptor, one can, in the foregoing manner, obtain a baseline activity for the recombinantly produced receptor. Then, to test for inhibitors or modifiers of the receptor function, one can incorporate into the admixture a candidate substance whose effect on the receptor is unknown. By comparing reactions which are carried out in the presence or absence of the candidate substance, one can then obtain information regarding the effect of candidate/receptor interaction on the receptor's normal function of regulation of a reporter construct.

Accordingly, it is proposed that this aspect of the present invention provides those of skill in the art with methodology that allows for the identification of candidate substances having the ability to modify the action of peroxisome proliferator-activated receptor polypeptides in one or more manners.

Additionally, screening assays for the testing of candidate substances are designed to allow the investigation of structure/activity relationships of ligands with the receptors, e.g., study of binding of naturally occurring hormones or other substances capable of interacting or otherwise modulating with the receptor versus studies of the activity caused by the binding of such molecules to the receptor. In certain embodiments, the polypeptides of the invention are crystallized in order to carry out x-ray crystallographic studies as a means of evaluating interactions with candidate substances or other molecules with the peroxisome proliferator-activated receptor polypeptide. For instance, the purified recombinant polypeptides of the invention, when crystallized in a suitable form, are amenable to detection of intra-molecular interactions by x-ray crystallography.

An important aspect of the invention is the use of recombinantly produced peroxisome proliferator-activated receptor polypeptide in screening assays for the identification of substances which can inhibit or otherwise modify or alter the function of the receptor. The use of recombinantly produced receptor is of particular benefit because the naturally occurring receptor is present in only small quantities and has proven difficult to purify. Moreover, this provides a ready source of receptor, which has heretofore been unavailable.

As described above, receptors in the presence of agonists exert their physiological effects through a secondary molecule. A screening assay of the invention, in preferred embodiments, conveniently employs a peroxisome proliferator-activated receptor polypeptide directly from the recombinant host in which it is produced. This is achieved most preferably by simply expressing the selected polypeptide within the recombinant host, typically a eukaryotic host, followed by preparing a crude homogenate which includes the enzyme. A portion of the crude homogenate is then admixed with an appropriate effector of the receptor along with the candidate substance to be tested. By comparing the binding of the selected effector to the receptor in the presence or absence of the candidate substance, one can obtain information regarding the physiological properties of the candidate substance.

The receptor can be expressed in a prokaryotic or a eukaryotic cell. Receptors have been expressed in E. coli (Bertin et al., 1992), in yeast (King et al., 1990) and in mammalian cells (Bouvier et al., 1988).

A cell expressing a receptor can be used whole to screen agents. For example, cells expressing the receptor of the present invention can be exposed to radiolabelled agent and the amount of binding of the radiolabelled agent to the cell can be determined.

The cell expressing the receptor can be fractionated into sub-cellular components which contain the receptor of the present invention. Methods for purifying sub-cellular fractions are well known in the art. Sub-cellular fractions include but are not limited to the cytoplasm, cellular membrane, other membranous fractions such as the endoplasmic reticulum, golgi bodies, vesicles and the nucleus. Receptors isolated as sub-cellular fractions can be associated with cellular membranes. For example, if cellular membrane vesicles are isolated from the cell expressing the receptor, the receptor molecule can be membrane bound. It is further contemplated that the receptor of the present invention can be purified from a cell that expresses the receptor. Methods of purification are well known in the art. The purified receptor can be used in screening assays.

There are believed to be a wide variety of embodiments which can be employed to determine the effect of the candidate substance on the receptor polypeptides of the invention, and the invention is not intended to be limited to any one such method. However, it is generally desirable to employ a system wherein one can measure the ability of the receptor polypeptide to bind to and or be modified by the effector employed in the presence of a particular substance.

The detection of an interaction between an agent and a receptor can be accomplished through techniques well known in the art. These techniques include but are not limited to centrifugation, chromatography, electrophoresis and spectroscopy. The use of isotopically labelled reagents in conjunction with these techniques or alone is also contemplated. Commonly used radioactive isotopes include $^3H$, $^{14}C$, $^{22}Na$, $^{32}P$, $^{35}S$, $^{45}Ca$, $^{60}Co$, $^{125}I$, and $^{131}I$. Commonly used stable isotopes include $^3H$, $^{13}C$, $^{15}N$, $^{18}O$.

For example, if an agent can bind to the receptor of the present invention, the binding can be detected by using radiolabelled agent or radiolabelled receptor. Briefly, if radiolabelled agent or radiolabelled receptor is utilized, the agent-receptor complex can be detected by liquid scintillation or by exposure to X-Ray film.

When an agent modifies the receptor, the modified receptor can be detected by differences in mobility between the modified receptor and the unmodified receptor through the use of chromatography, electrophoresis or centrifugation. When the technique utilized is centrifugation, the differences in mobility is known as the sedimentation coefficient. The modification can also be detected by differences between the spectroscopic properties of the modified and unmodified receptor. As a specific example, if an agent covalently modifies a receptor, the difference in retention times between modified and unmodified receptor on a high pressure liquid chromatography (HPLC) column can easily be detected.

As a specific example, if an agent covalently modifies a receptor, the spectroscopic differences between modified and unmodified receptor in the nuclear magnetic resonance (NMR) spectra can be detected. Alternatively, one can focus on the agent and detect the differences in the spectroscopic properties or the difference in mobility between the free agent and the agent after modification of the receptor.

When a secondary polypeptide is provided, the agent-receptor-secondary polypeptide complex or the receptor-secondary polypeptide complex can be detected. Differences in mobility or differences in spectroscopic properties as described above can be detected.

It is further contemplated that when a secondary polypeptide is provided the enzymatic activity of the effector polypeptide can be detected. For example, many receptors exert physiological effects through the stimulation or inhibition of adenylyl cyclase. The enzymatic activity of adenylyl cyclase in the presence of an agent can be detected.

The interaction of an agent and a receptor can be detected by providing a reporter gene. Well known reporter genes include β-galactosidase (β-Gal), chloramphenicol transferase (CAT) and luciferase. The reporter gene is expressed by the host and the enzymatic reaction of the reporter gene product can be detected.

In preferred assays, an admixture containing the polypeptide, effector and candidate substance is allowed to incubate for a selected amount of time, and the resultant incubated mixture subjected to a separation means to separate the unbound effector remaining in the admixture from any effector/receptor complex so produced. Then, one simply measures the amount of each (e.g., versus a control to which no candidate substance has been added). This measurement can be made at various time points where velocity data is desired. From this, one can determine the ability of the candidate substance to alter or modify the function of the receptor.

Numerous techniques are known for separating the effector from effector/receptor complex, and all such methods are intended to fall within the scope of the invention. Use of thin layer chromatographic methods (TLC), HPLC, spectrophotometric, gas chromatographic/mass spectrophotometric or NMR analyses. It is contemplated that any such technique can be employed so long as it is capable of differentiating between the effector and complex, and can be used to determine enzymatic function such as by identifying or quantifying the substrate and product.

A. Screening Assays for Peroxisome Proliferator-activated Receptor Polypeptides.

The present invention provides a process of screening a biological sample for the presence of a peroxisome proliferator-activated receptor polypeptide. A biological sample to be screened can be a biological fluid such as extracellular or intracellular fluid or a cell or tissue extract or homogenate. A biological sample can also be an isolated cell (e.g., in culture) or a collection of cells such as in a tissue sample or histology sample. A tissue sample can be suspended in a liquid medium or fixed onto a solid support such as a microscope slide.

In accordance with a screening assay process, a biological sample is exposed to an antibody immunoreactive with the peroxisome proliferator-activated receptor polypeptide whose presence is being assayed. Typically, exposure is accomplished by forming an admixture in a liquid medium that contains both the antibody and the candidate peroxisome proliferator-activated receptor polypeptide. Either the antibody or the sample with the peroxisome proliferator-activated receptor polypeptide can be affixed to a solid support (e.g., a column or a microtiter plate).

The biological sample is exposed to the antibody under biological reaction conditions and for a period of time sufficient for antibody-polypeptide conjugate formation. Biological reaction conditions include ionic composition and concentration, temperature, pH and the like.

Ionic composition and concentration can range from that of distilled water to a 2 molal solution of NaCl. Preferably, osmolality is from about 100 mosmols/l to about 400 mosmols/l and, more preferably from about 200 mosmols/l to about 300 mosmols/l. Temperature preferably is from about 4° C. to about 100° C., more preferably from about 15° C. to about 50° C. and, even more preferably from about 25° C. to about 40° C. pH is preferably from about a value of 4.0 to a value of about 9.0, more preferably from about a value of 6.5 to a value of about 8.5 and, even more preferably from about a value of 7.0 to a value of about 7.5. The only limit on biological reaction conditions is that the conditions selected allow for antibody-polypeptide conjugate formation and that the conditions do not adversely affect either the antibody or the peroxisome proliferator-activated receptor polypeptide.

Exposure time will vary inter alia with the biological conditions used, the concentration of antibody and polypeptide and the nature of the sample (e.g., fluid or tissue sample). Means for determining exposure time are well known to one of ordinary skill in the art. Typically, where the sample is fluid and the concentration of polypeptide in that sample is about $10^{-10}$ M, exposure time is from about 10 minutes to about 200 minutes.

The presence of peroxisome proliferator-activated receptor polypeptide in the sample is detected by detecting the formation and presence of antibody-peroxisome proliferator-activated receptor polypeptide conjugates. Means for detecting such antibody-antigen (e.g., receptor polypeptide) conjugates or complexes are well known in the art and include such procedures as centrifugation, affinity chromatography and the like, binding of a secondary antibody to the antibody-candidate receptor complex.

In one embodiment, detection is accomplished by detecting an indicator affixed to the antibody. Exemplary and well known such indicators include radioactive labels (e.g., $^{32}P$, $^{125}I$, $^{14}C$), a second antibody or an enzyme such as horse radish peroxidase. Means for affixing indicators to antibodies are well known in the art. Commercial kits are available.

B. Screening Assay for Anti-peroxisome Proliferator-activated Receptor Antibody.

In another aspect, the present invention provides a process of screening a biological sample for the presence of antibodies immunoreactive with a peroxisome proliferator-activated receptor polypeptide (i.e., an anti-peroxisome proliferator-activated receptor antibody). In accordance with such a process, a biological sample is exposed to a peroxisome proliferator-activated receptor polypeptide under biological conditions and for a period of time sufficient for antibody-polypeptide conjugate formation and the formed conjugates are detected.

C. Screening Assay for Polynucleotide that Encodes a Peroxisome Proliferator-activated Receptor Polypeptide.

A DNA molecule and, particularly a probe molecule, can be used for hybridizing as oligonucleotide probes to a DNA source suspected of possessing a peroxisome proliferator-activated receptor polypeptide encoding polynucleotide or gene. The probing is usually accomplished by hybridizing the oligonucleotide to a DNA source suspected of possessing such a receptor gene. In some cases, the probes constitute only a single probe, and in others, the probes constitute a collection of probes based on a certain amino acid sequence or sequences of the peroxisome proliferator-activated receptor polypeptide and account in their diversity for the redundancy inherent in the genetic code.

A suitable source of DNA for probing in this manner is capable of expressing peroxisome proliferator-activated receptor polypeptides and can be a genomic library of a cell line of interest. Alternatively, a source of DNA can include total DNA from the cell line of interest. Once the hybridization process of the invention has identified a candidate DNA segment, one confirms that a positive clone has been obtained by further hybridization, restriction enzyme mapping, sequencing and/or expression and testing.

Alternatively, such DNA molecules can be used in a number of techniques including their use as: (1) diagnostic tools to detect normal and abnormal DNA sequences in DNA derived from patient's cells; (2) means for detecting and isolating other members of the peroxisome proliferator-activated receptor family and related polypeptides from a DNA library potentially containing such sequences; (3) primers for hybridizing to related sequences for the purpose of amplifying those sequences; (4) primers for altering the native peroxisome proliferator-activated receptor DNA sequences; as well as other techniques which rely on the similarity of the DNA sequences to those of the peroxisome proliferator-activated receptor DNA segments herein disclosed.

As set forth above, in certain aspects, DNA sequence information provided by the invention allows for the preparation of relatively short DNA (or RNA) sequences (e.g., probes) that specifically hybridize to encoding sequences of the selected peroxisome proliferator-activated receptor gene. In these aspects, nucleic acid probes of an appropriate length are prepared based on a consideration of the selected peroxisome proliferator-activated receptor sequence (e.g., a sequence such as that shown in SEQ ID NO: 1). The ability of such nucleic acid probes to specifically hybridize to peroxisome proliferator-activated receptor encoding sequences lend them particular utility in a variety of embodiments. Most importantly, the probes can be used in a variety of assays for detecting the presence of complementary sequences in a given sample. However, uses are envisioned, including the use of the sequence information for the preparation of mutant species primers, or primers for use in preparing other genetic constructions.

In certain embodiments, it is advantageous to employ a nucleic acid sequence of the present invention in combination with an appropriate means, such as a label, for determining hybridization. A wide variety of appropriate indicator means are known in the art, including radioactive, enzymatic or other ligands, such as avidin/biotin, which are capable of giving a detectable signal. In preferred embodiments, one likely employs an enzyme tag such a urease, alkaline phosphatase or peroxidase, instead of radioactive or other environmentally undesirable reagents. In the case of enzyme tags, calorimetric indicator substrates are known which can be employed to provide a means visible to the human eye or spectrophotometrically, to identify specific hybridization with complementary nucleic acid-containing samples.

X. Screening Assay Kits

In another aspect, the present invention contemplates a diagnostic assay kit for detecting the presence of a peroxisome proliferator-activated receptor polypeptide in a biological sample, where the kit comprises a first container containing a first antibody capable of immunoreacting with a peroxisome proliferator-activated receptor polypeptide, with the first antibody present in an amount sufficient to perform at least one assay. Preferably, an assay kit of the invention further comprises a second container containing a second antibody that immunoreacts with the first antibody. More preferably, the antibodies used in an assay kit of the present invention are monoclonal antibodies. Even more preferably, the first antibody is affixed to a solid support. More preferably still, the first and second antibodies comprise an indicator, and, preferably, the indicator is a radioactive label or an enzyme.

In an alternative aspect, the present invention provides a diagnostic assay kit for detecting the presence, in biological samples, of a polynucleotide that encodes a peroxisome proliferator-activated receptor polypeptide, the kits comprising a first container that contains a second polynucleotide identical or complementary to a segment of at least 10 contiguous nucleotide bases of SEQ ID NO:1.

In another embodiment, the present invention contemplates a diagnostic assay kit for detecting the presence, in a biological sample, of an antibody immunoreactive with a peroxisome proliferator-activated receptor polypeptide, the kit comprising a first container containing a peroxisome proliferator-activated receptor polypeptide that immunoreacts with the antibody, with the polypeptide present in an amount sufficient to perform at least one assay.

EXAMPLES

Examples have been included to illustrate preferred modes of the invention. Certain aspects of the following examples are described in terms of techniques and procedures found or contemplated by the present inventors to work well in the practice of the invention. These examples are exemplified through the use of standard laboratory practices of the inventor. In light of the present disclosure and the general level of skill in the art, those of skill will appreciate that the following examples are intended to be exemplary only and that numerous changes, modifications and alterations can be employed without departing from the spirit and scope of the invention.

Example 1

Cloning and Sequence of Human PPAR-γ

Generation and Screening of Human Bone Marrow cDNA Library.

Oligo(dT)-primed first strand cDNA was prepared from 2.6 μg poly A selected normal human bone marrow aspirate RNA (see below). The oligo (dT) primer (5'ACTAGTGCGGCCGCCTAGGCCTCGAGTTTTTTT TTTTTTTT 3') (SEQ ID NO:3) (Blumberg et al., 1992) was used to create an oriented library, by a modified method of Blumberg (Blumberg et al., 1992). 5-methyl dCTP was incorporated during first strand synthesis to protect internal Xho 1 sites by hemi-methylation interference. Residual 5 methyl dCTPs were removed and second strand synthesis was performed, incorporating the 3' Xho 1 site. Internal EcoRI sites were then protected by EcoRI methylase treatment, the cDNA ends were made blunt-ended, and EcoRI linkers were added. After combined EcoRI and Xho 1 digestion, the cDNA was purified by Sepharose CL-4B chromatography to remove linkers and size fractionate the cDNA. Double stranded cDNAs, approximately 500 base pairs or greater, were ligated to λ ZAP II arms (Stratagene) and packaged in vitro with Gigapack II Gold (Stratagene). This library contained $7.4 \times 10^7$ independent clones and was screened unamplified.

The library was screened in duplicate with an HPLC-purified $^{32}$P-labeled synthetic 512 fold-degenerate oligonucleotide (TGYGARGGNTGYAARGGNTTYTT) (SEQ ID NO:4) (Blumberg et al., 1992) under low stringency conditions (1M NaCl, 0.1 M Tris-HCl pH 8.0, 6 mM EDTA, 125 units of heparin per ml, 0.05% sodium dodecyl sulfate, at 46C) and washed at high stringency (two 15 minute room temperature washes, one in 6×SSC/0.05% sodium pyrophosphate, and one in 3 M tetramethylammonium chloride/0.05 M Tris-HCl pH 8.0/0.2 mM EDTA (3M TMAC), two 20 minute washes at 58 C in 3 M TMAC, then one 15 minute wash at room temperature in 6×SSC/0.05% sodium pyrophosphate). This oligonucleotide (Blumberg et al., 1992) is a mixture of all possible DNA sequences encoding the highly conserved amino acid sequence CEGCKGFF (SEQ ID NO:5), found in the first cysteine finger of the members of the thyroid-retinoid branch of the nuclear receptor superfamily (Wahli and Martinez, 1991; Evans, 1988). Positive plaques from the initial high density screen of $1 \times 10^6$ clones were purified on secondary and tertiary screens, then converted to plasmids by the automatic excision process (Stratagene Unizap) (Short et al., 1988). Purified plasmids were sequenced using a modified dideoxy chain termination method (Tabor and Richardson, 1989), and the screening oligonucleotide as the initial primer. Clones identified as either similar to or members of the thyroid retinoid branch of the nuclear receptor superfamily were further characterized.

DNA sequences were analyzed using programs of Staden (Staden, 1986), University of Wisconsin Genetics Computer Group (Devereaux, 1984), Feng and Doolittle (Feng and Doolittle, 1987), DNASIS (Hitachi), GeneWorks release 2.2 (IntelliGenetics) and DNA Strider release 1.0 (Commissariat a l'Energie Atomique, France).

Northern hybridizations: Prehybridizations and hybridizations were performed in 7% SDS, 0.5 M $Na_2PO_4$ pH 7.2 with 100 μg/ml salmon sperm DNA at high stringency (65 C) [15]. Double stranded, denatured cDNA fragments obtained by band preparation from agarose gels, ranging in size from 400–1600 bp were used as probes. These probes were random prime labeled with $P^{32}$ α dCTP, with specific activities from $0.4$–$1.0 \times 10^9$ cpm/μg (Pharmacia Oligolabelling kit), and used at concentrations of 3 to $5 \times 10^6$ cpm per ml of hybridization solution. Exposures ranged from overnight to 10 days with Kodak XAR film and 3 Dupont Quanta III screens at −70 C.

Preparation of RNA.

Bone marrow aspirate RNA: 30 cc of normal bone marrow was aspirated from a single site from the posterior iliaccrest of a normal volunteer with a Jamshidi needle and standard sterile procedures. The aspirate was immediately placed on ice, and after clotting, 7 cc of serum was removed and the remainder of the sample was transferred rapidly to 50 cc sterile tubes with 1.5 volumes of 4 M Guanidine isothiocyanate solution (4 M guanidine isothiocyanate, 0.5% N-lauroylsarcosine, 25 mM sodium citrate, 0.1 M 2-mercaptoethanol). Samples were immediately homogenized with a NaOH cleaned high speed (Polytron) tissue homogenizer, and RNA prepared using a modified Chirgwin procedure (Chirgwin et al., 1979). The 360 μg total RNA sample was stored in ethanol at −20 C. until Poly A selected.

Poly A selection: 200 μg of bone marrow aspirate total RNA was poly A selected according to a method by Cho (Wahli and Martinex, 1991). The integrity of the 9 μg of poly A selected RNA obtained was confirmed by gel electrophoresis.

Fractionated peripheral blood cell total and poly A RNA isolation: A leukapheresis pack was obtained from the American Red Cross. Monocytes, lymphocytes and neutrophils were separated by standard procedures (Kitano et al., 1991) with the monocytes and lymphocytes separated by overnight adherence. The neutrophil pellet yielded 106 μg of poly A RNA using the procedure described above. Monocytes separated by standard procedures (Kitano e al., 1991) were scraped gently off plates and pelleted, yielding 13 μg total RNA by the above procedure. Monocytes were isolated from three leukapheresis packs by Ficoll-Paque (Pharmacia) separation (Kitano et al., 1991), followed by overnight adherence in Iscove's modified Dulbecco's media (Gibco) with 15% fetal bovine serum (Gemini) and 5% heat inactivated human AB serum at 37 C. Cells were lysed in situ on the plates with 4 M Guanidine. 5 μg poly A RNA was prepared from the total RNA using the Fastrack kit (Invitrogen). Lymphocyte total RNA and poly A selected RNA were obtained from Ficoll-Paque (Pharmacia) separated fractions using the same procedures described above.

Cell line RNA: The following human hematopoietic cell lines were used for RNA and DNA preparation: T cell: CCRF-HSB-2, CCRF-CEM, MOLT-4, JURKAT B Cell:-Raji, NOR 25 (an EBV transformed normal adult peripheral blood B cell line kindly provided by Nancy Perillo) murine pre B: 18.81, Wehi 231,70Z3, (kindly provided by O. Witte) Myeloid: HL60, KG-1, K562, THP-1.

All cells were cultured in Iscove's modified Dulbecco's medium (Gibco) with 10% fetal bovine serum (Gemini), 100 μ/ml penicillin G, 0.1 mg/ml streptomycin (Sigma, L-glutamine 0.4 mM (Gibco). The NOR-25, THP-1, 18.81, Wehi 231, and 70Z3 cell lines had $5 \times 10^{-5}$ M β mercaptoethanol (Gibco) added. NOR-25 also required 0.01 M Hepes (Gibco). A quantity of 20–40 μg of Poly A selected RNA was made from $1 \times 10^8$ cells using the Fastrack kit (Invitrogen).

Sequence of Human PPAR-γ Clones.

Two PPAR-γ clones were identified from the degenerate oligonucleotide screen of the normal human bone marrow cDNA library. Both share a significant percentage of amino acid identity with the PPAR family of gene products, and especially with xenopus PPAR-γ (see below). These two clones, one full-length (clone 14) and one incomplete (clone 22) are therefore identified as human versions of the PPAR-γ gene.

The full length PPAR-γ cDNA (clone 14), was isolated and sequenced from both ends. This clone was 1844 bp long, with the open reading frame beginning at bp 179, and the stop codon at bp 1604. The 1428 BP open reading frame encodes a 476 amino acid nuclear receptor protein, with a molecular weight of approximately 54.2 kDa. The beginning of the A/B region contains the amino acid sequence MVDT, as has been reported for other members of this family. Clone 14 contains all functional components characteristic of nuclear receptors, and shows similarities and conservative base changes with the human NUC 1 receptor, the murine and rat PPAR-α, and the xenopus PPAR α, β and γ receptors. Clone 14 shows the greatest similarity (73% overall amino acid identify) to the xenopus PPAR-γ cDNA (FIG. 1).

Sequencing of the second clone (clone 22) revealed an artifactural splice at a Hind III site (bp 597) in the C region, causing abrupt loss of 9 highly conserved C region amino acids. The next 1247 bp's are identical to clone 14, confirming the majority of the sequence obtained from the full length receptor contained in clone 14.

Example 2 mRNA Expression Studies

Isolation of bone marrow stromal cells: Bone marrow stromal cells were obtained from a normal donor bone marrow harvest, filtered through a 200 micron wire mesh screen, washed with saline and suspended in Dexter's media, (cells kindly donated by J. Nolta and D. Kohn, M.D., L.A. Children's Hospital). Cells were maintained in DOM (IMDM, 15% horse serum, 15% fetal calf serum, $5 \times 10^{-5}$ M β mercaptoethanol, $10^{-3}$ M hydrocortisone, with pen/strep) for 2 additional passages (total of 4 passages) before harvesting. Collagenase was used during passaging of the cells to allow cells to retain their capability to differentiate towards adipose as well as fibroblastic cell types (Nolta et al., 1992). Poly A mRNA was obtained from $1 \times 10^8$ cells using the Fastrack kit.

Patient samples: Patients seen at UCLA with acute leukemia or chronic myelogenous leukemia provided informed consent to donate blood, as approved by the UCLA Human Subject Protection Committee. Fifteen to 30 ml of peripheral blood was obtained from patients with active leukemia and the mononuclear cell fraction was isolated by Ficoll-Hypaque density separation. Total RNA was prepared according to a modification of the Chirgwin method (Chirgwin et al., 1979).

Fetal RNA: Tissue samples from fetuses with no known genetic abnormality or chemical exposure were provided by elective surgical abortions performed between 11–24 weeks postconception, after obtaining the patient's informed consent. Samples were obtained within minutes of pregnancy termination and were frozen immediately in liquid nitrogen and stored at −80 C. The conceptional age of abortuses was determined by measurement of fetal foot length (Moore, 1982). Prior to freezing, samples of fetal cortex were dissected away from the central diencephalon and the basal ganglia, and were freed of membrane and choroid plexus; the meninges were removed from spinal cords. Samples of placental tissue were obtained from the fetal aspect following removal of the amnion and chorion.

RNA was prepared from fetal cortex, cerebrum, pooled intact and partial spinal cords, kidney, lung, placenta and liver. Total RNA was prepared from frozen tissue fragments by homogenization in GITC using the methods of Chirgwin et al (Chirgwin et al., 1979) or Chomczynski and Sacchi (Chomczynski and Sacchi, 1987). An RNA fraction enriched in poly A+ RNA was isolated from total RNA by affinity chromatography (Avid and Leder, 1972). Preparation of an additional northern blot containing fetal liver RNA was previously described (Kronquist et al., 1990).

Northern blots: Formaldehyde 0.66 M to 2.0 M, agarose 1%, 1× MOPs gels were loaded with either methyl mercury or heat denatured total cellular or poly A selected RNA. Gels were transferred to either Hybond (Amersham) or Nytran (Schleicher and Schuell) membranes using standard platform transfer techniques in 10× or 20×SSC.

Northern blot analysis was performed to examine the pattern of expression of this transcription factor in hematopoietic and bone marrow stromal cells. Expression of two different PPAR-γ mRNA transcripts was observed in hematopoietic cells. Two PPAR-γ transcripts of similar size are also present in the xenopus system [12]. The human 1.85 kb transcript is large enough to contain all the functional regions present in the 1428 base pair open reading frame cDNA sequence cloned from the bone marrow library. The 0.65 kb transcript by size alone cannot contain all the functional regions of a nuclear receptor (e.g. the ligand binding domain is 678 bp, the DNA binding domain is 196 bp and a short linker region would be 220–234 bp for a total 1.1 kb). The partial clone (clone 22) was not considered to represent the short 650–700 bp transcript based on length, since it contained 1247 bps with 1010 bps identical to clone 14 full length receptor open reading frame.

The larger transcript (PPAR-γ 1) is expressed in a variety of malignant hematopoietic cell lines, normal peripheral blood monocytes cultured overnight, and primary cultured stromal cells. (See Table 1.) The shorter 0.65 kb transcript (PPAR-γ 2) is the only form seen in circulating peripheral blood neutrophil and lymphocyte fractions, as well as in circulating mononuclear cells from patients with acute lymphocytic leukemia and acute and chronic myeloid leukemia. No. PPAR-γ mRNA was detected in Jurkat, HSB, Raji, K562, or KG-1 cell lines.

Expression of only the smaller transcript was detected in the peripheral blood of adult patients with acute myeloid leukemia (AML), chronic myeloid leukemia (CML), CML in blast crisis and acute lymphocytic leukemia (ALL). Not all patient samples showed expression of PPAR-γ. Blast counts varied somewhat, and it was considered that some of the signal could have been generated by the few normal lymphocytes or monocytes remaining after a Ficoll-hypaque separation. However, 20 μg total RNA from normal peripheral blood lymphocytes shows no signal under the same hybridization conditions.

A 5-μg poly A selected RNA was obtained from peripheral blood monocytes separated from lymphocytes by overnight adherence in Iscove's media supplemented with 15% fetal calf serum. The dominant signal is the long PPAR-γ 1 transcript. The short transcript signal may be from contaminating lymphocytes, a subpopulation of monocytes such as activated monocytes or macrophages, or coexpressed in the same cells as the long transcript.

Primary bone marrow stromal cells cultured for a total of 4 passages expressed only the 1.8 kb (PPAR-γ 1) transcript. In contrast to isolated hematopoietic cell populations, other human organ systems show expression of both transcripts, (colon, bladder, kidney, skeletal muscle, liver, spleen, placenta, and stomach) with the 1.85 kb mRNA being dominant in colon, muscle, placenta and bladder. Both transcripts were also seen in fetal organs (16–19 gestational weeks) with varying ratios of each transcript in fetal cerebral cortex, lung (very faint) and kidney. The 1.85 kb transcript was dominant in fetal kidney, and the 0.67 transcript was dominant in fetal liver and lung.

Normal peripheral blood lymphocytes, polymorphonuclear leukocytes, and circulating leukemia cells from patients with ALL, CML, and CML in blast crisis, express only the shorter 0.65 kb PPAR-γ transcript. In contrast, hematopoietic leukemia cell lines derived from acute myeloid leukemia (HL60-M3, U937 and THP-1, monocytic/histiocytic with FC receptors and phagocytic capabilities) express only the 1.85 kb mRNA, as detected by northern blot analysis. Cultured stromal cells also only express the 1.85 kb transcript, indicating that some aspect of culture conditions, such as rapid cell division, and/or increased utilization of fatty acid B or ω oxidation pathways may be reflected in PPAR-γ transcription. Another consideration is that the ligand for PPAR is likely to be a product of eicosanoid metabolism (Gottlicher et al., 1992; Muerhoff et al., 1992). Many types of eicosanoid metabolism in the peripheral blood compartment require the concurrent presence of more than one cell type (Marcus, 1990). Platelets, neutrophils, and erythrocytes may participate in this eicosanoid transcellular metabolism. For example, 5-HETE is produced by neutrophils from platelet derived precursors. This can account for the fact that an eicosanoid metabolite binding transcription factor regulating a key enzyme of eicosanoid ω oxidation is transcribed differently in the peripheral blood compartment than it is in tissue culture. Other differences involve growth factors. Overnight culture of human leukemia cells induce high levels of II-1, which can induce the in vitro expression of the myeloid growth factor GM-CSF [Kaufman, 1988 #57]. The peripheral blood monocyte fraction which also expressed predominately the 1.85 kb transcript was exposed to Iscove's media with 15% fetal bovine serum overnight during separation by adherence. All cultured cell lines were exposed to 10% fetal calf serum. In contrast, the leukemic cells fresh from patient peripheral blood, with manipulations other than ficoll separation, show expression of only the short transcript.

In examining the lymphoid lineage, it is apparent that peripheral blood lymphocytes (95% T) and ALL circulating blasts express short PPAR-γ 2 transcript, while neither of the two T lymphoid cells lines studied (HSB and Jurkat) expressed any PPAR transcript. Normal peripheral blood B cells transformed with Epstein Barr virus in culture expressed the long transcript. In acute myeloid leukemia, cell lines (HL60, THP-1, U937,) expressed the long PPAR-γ 1 transcript, and some fresh acute myeloid leukemic cells produced the short PPAR-γ 2 transcript.

The main purpose of examining the leukemic patient peripheral blood samples was to ascertain if PPAR-γ expression was restricted to any diagnostic category. PPAR-γ expression of the short transcript was seen in ALL, CML, and AML. Whether the presence or absence of PPAR-γ expression correlates with any clinical parameter is difficult to determine with currently available data.

PPAR-γ has novel regulatory aspects and appears to be widely expressed in the human hematopoietic system, and in a variety of both adult and fetal organs. The ratio of the two transcripts, 1.85 kb (PPAR-γ 1) and 0.65 kb (PPAR-γ 2) vary from organ to organ, and a detailed study of the hematopoietic system suggests that different populations of cells in an organ system may express one transcript or the other preferentially.

Previous studies of PPARs have focused on the expression of all three PPARs in the xenopus system (Dreyer et al., 1992), existence of PPAR alpha in humans (Sher et al., 1993) and rats (Gottlicher et al., 1992), and expression of PPAR alpha in murine systems [Beck, 1992 #25; Issemann et al., 1990; Tugwood et al., 1992]. XPPAR-γ expression is seen in xenopus oocytes, liver, kidney and abdominal body fat. It appears the hPPAR-γ is expressed in a great variety of human organ systems.

Sac I, Taq I, Pvu II, Pst I, Bgl II, Msp I, EcoR V, and Kpn I. DNA fragments were fractionated by 0.7 or 0.8% agarose gel electrophoresis, and transferred to positively charged nylon membranes in 0.5 N NaOH as described. A 1.6 kb full length hPPAR-γ, and a plasmid control probe were used for cell line southern blot analyses. A 0.8 kb A, B, C, and D region hPPAR-γ probe was used for hybridization to normal volunteer DNA for Southern blot RFLP analyses. Probes were labelled as described above. The membranes were

TABLE 1

| LINEAGE | NAME | PPARγ1 (1.85 kb) | PPARγ2 (0.65 kb) | RAR a (3.6/2.4 kb) |
|---|---|---|---|---|
| Cultured Malignant Hematopoietic Cell Lines | | | | |
| Lymphoid | | | | |
| T-Lymphoblastoid | HSB-2 | – | – | +++ |
| | MOLT-4F | – | – | +++ |
| | CCRF-CEM | – | – | +++ |
| T-cell | JURKAT | – | – | +++ |
| B-cell (Burkitts) | RAJI | – | – | +++ |
| B-cell (peripheral blood, EBV transformed) | NOR-25 | +++ | – | +++ |
| Myeloid | | | | |
| Promyelocytic | HL60 | +++ | – | +++ |
| Myeloid-monocytic | U937 | +++ | – | +++ |
| (histiocytic, FC | THP-1 | +++ | – | +++ |
| receptors, phago- | KG-1 | – | – | +++ |
| cytic, AML) | | | | |
| Erythroid | | | | |
| Myeloid-Erythroid heme + expression | K562 | – | – | +++ |
| Peripheral Blood, Bone Marrow Compartments | | | | |
| Peripheral blood, | PMNs | – | ++++ | ++++++++ |
| (fractionated, normal) | Lymphocytes (95% T) | – | +++ | +++ |
| | Monocytes (adherence purified, in culture overnight | + | ++ | +++ |
| Total bone marrow aspirate stroma/hematopoietic cells | | +++ | + | +++ |
| Cultured primary bone marrow cells, fibroblastic and adipocytic differentiation | | +++ | – | +++ |
| Peripheral Bld/Leukemic Pts. | | | | |
| AML | M1 | 0/2– | 0/2– | ND |
| | M2 | 0/4– | 2/4+ | ND |
| | M3 | ND | ND | ND |
| | M4 | 0/2– | 1/2+ | ND |
| | M5 | 0/1– | 1/1+ | ND |
| | Unspecified | 0/2– | 1/2+ | ND |
| CML | | 0/8– | 7–8+ | ND |
| CML in blast crisis | | 0/5– | 1/5+ | ND |
| ALL | L1 | 0/1– | 1/1+ | ND |
| | L2 | 0/4– | 2/4+ | ND |
| | bi-phenotypic | 0/2– | 2/2+ | ND |
| | NK cell, TDT- | 0/1+ | ?1/1+ | ND |

Example 3

Genomic Alterations

Southern blot analysis: Genomic DNA was isolated from peripheral blood leukocytes of 10 normal volunteers, from 13 cell lines, and normal primary cultured bone marrow stromal cells (Gatti et al., 1989; McBride et al., 1989). 5 mg of cell line and stromal cell DNA was digested to completion with EcoR I, Bam HI, and Hind III restriction enzymes for the cell line southerns under conditions specified by the supplier. DNA from the normal volunteers was digested with restriction endonucleases EcoR I, Bam HI, Hind III, Xba I, hybridized (at 42° C. in 50% formamide) and washed (in 0.1×SSC at 55–58° C.) at high stringency allowing less than 10% sequence divergence as described (McBride et al., 1989).

Somatic Cell Hybrids: The isolation and characterization of a panel of human-rodent somatic cell hybrids retaining subsets of human chromosomes has been described previously (McBride et al., 1982). Hybrid cell lines were characterized for the presence of all human chromosomes except Y by standard isoenzyme analyses, by Southern analysis with probes from previously localized genes, and frequently, by cytogenetic analysis.

Linkage analysis: Southern blots of Xba I digests of DNAs from 40 large, three-generation CEPH families (Dausset et al., 1990) were used for hybridization with a 0.8 kb A/B, C and D region hPPAR-γ cDNA probe. RFLP typing was performed by standard Southern blot analysis under high stringency conditions. All parental DNAs were initially examined, and all family members from informative matings (i.e., those with one or both heterozygous parents) were then examined. Two-point and multipoint linkage analysis of PPAR-γ versus loci typed in the CEPH database version 5 were performed using LINKAGE version 5.1 for microcomputers (Lathrop et al., 1984). An infrequent Taq I polymorphism (B1:B2=7.1:5.3kb) detected in one CEPH parent was used to genotype CEPH family 1413 and the results with Xba I and Taq I were combined as a haplotype in this family.

Chromosomal Localization of hPPAR-γ: The gene was localized by Southern blot analysis of a panel of EcoRI-digested human-rodent somatic cell hybrid DNAs with a hPPAR-γ cDNA probe. The three hybridizing bands in human DNAs were readily distinguished from cross-hybridizing bands in rodent DNAs (not shown). All human bands co-segregated and the gene could be unambiguously assigned to human chromosome 3 and it segregated discordantly (>18%) with all other human chromosomes. The gene was further localized on the short arm of chromosome 3 by examination of two hybrids containing spontaneous breaks or deletions involving this chromosome. One hybrid contained a large deletion in the short arm with loss of distal 3p markers RAF1 (3p25), THRB (3p24.1-p22), and ACY1 (3p21), but retention of DNF15S2 (3p21.2–21.3), CCHL1A2 (3p14.3) (Chin et al., 1991) as well as two other more centromeric 3p markers and all loci on 3q. The other hybrid contained a break in proximal 3q with retention of long arm markers and loss of all short arm markers. The hPPAR-γ gene was absent from both of these hybrids indicating that it must be located in the region 3p21-p25.

The gene could be further localized to band 3p25 by genetic linkage analysis after identification of a high frequency RFLP at the hPPAR-γ locus (PPARG). The 0.8 kb hPPAR-γ cDNA probe was used for blot hybridization with genomic DNAs, and an RFLP was detected in Xba I digests with this probe. Allelic bands of 4.0 kb (A2) and 9.0 kb (A1) were found in addition to constant bands of 3.0, 4.4, and 7.2 kb lengths. In 80 CEPH parents, the allele frequencies were: A1:A2=0.5:0.5. The Xba I polymorphism was used for linkage analysis in the CEPH families. One or both parents was a heterozygote in 34 of the 40 total families, and both parents were heterozygotes in 18 of these families. All family members were examined in the informative families and the genotypes were entered into the CEPH database and used for linkage analysis with other published markers from chromosome 3p. Several errors were detected and corrected.

Multipoint linkage analysis of PPARG with other published markers (Tory et al., 1992) in the 3p26-p22 region was used to order PPARG with respect to these other loci. The results do not permit ordering of PPAR-γ and RAF1, but both loci are centromeric to D3S18 and telomeric to D3S588 and THRB, within band 3p25.

Genomic alterations: Southern blot analysis was performed to investigate PPAR-γ gene integrity in those cell lines that did not express PPAR-γ. Two of the five cell lines which did not express PPAR-γ transcripts (Raji and Jurkat) had major genomic alterations. The increase in intensity of two of the bands seen on the Eco RI, Bam HI, and Hind III digests of Raji cell genomic DNA, relative to the respective germline bands, is suggestive of amplification of an abnormal gene arrangement. The deletions seen in the Jurkat cells are consistent with abnormalities (deletions) of 3p previously identified in these cells[50] consistent with the localization of the hPPAR-γ gene. The other three cell lines (HSB, K562, and KG-1) showed normal germline patterns. Polymorphism studies in CEPH families and other southern blot studies demonstrated that the patterns seen in Jurkat and Raji are not consistent with natural polymorphisms.

Because numerous modifications and variations in the practice of the present invention are expected to occur to those skilled in the art, only such limitations as appear in the appended claims should be placed thereon.

References Cite

The references listed below as well as all references cited in the specification are incorporated herein by reference to the extent that they supplement, explain, provide a background for or teach methodology, techniques and/or compositions employed herein.

Adelman et al., DNA 2:183 (1983).
Agura, et al., Blood, 79:602–609 (1992).
Antibodies "A Laboratory Manual, E. Howell and D. Lane, Cold Spring Harbor Aronica Laboratory, (1988).
Avid et al., Proc. Natl. Acad. Sci USA, 69:1408–1412 (1972).
Beck et al., Proc. R. Soc. London B 247: 83–87 (1992).
Beier et al., European Journal of Cell Biology 46:383–393 (1988).
Berioli et al., Cardiologia 35: 335–340 (1990).
Bertin et al., J. Biol. Chem. 267(12):8200 (1992).
Blaauboer et al., Biochemical Pharmacology, 40:521–528 (1990).
Blumberg et al., Natl. Acad. Sci. USA, 89:2321–2325 (1992).
Bolivar et al., Gene, 2:95 (1977).
Boshart et al., Cell 41:521 (1985).
Bouvier et al., Mol. Pharmacol. 33:133 (1988).
Cattley et al., Cancer Res. 49: 3246–3251 (1989).
Chang et al., Nature, 375:615 (1978).
Chin et al., Genomics 11:914–919 (1991).
Chirgwin et al., Biochemistry, 18:5294–5299 (1979).
Chomczynski et al., Anal. Biochemistry, 162:156–159 (1987).
Crea et al., Proc. Natl. Acad. Sci. U.S.A, 75:5765 (1978).
Danboldt et al., Biochemistry 29(28):6734 (1990).
Danielian et al., EMBO, 11:1025–1033 (1992).
Dausset et al., Genomics 6:575–577 (1990).
Debois et al., Cell 67:731–740 (1991).
Devereaux et al., Nucleic Acids Research, 12:387–395 (1984).
Dreyer et al., Cell, 68:879–887 (1992).
Eacho et al., Toxicol. Appl. Pharmacol. 83: 430–437 (1986).
Elder et al., J. Invest. Derm. 96: 425–433 (1991).
Evans, Science, 240:889–895 (1988).
Feng et al., J. Mol Evolution, 25:351–36 (1987).
Ferruti et al., Crit. Rev. Ther. Drug Carrier Syst. 2:117–136 (1986).
Fiers et al., Nature 273:113 (1978).
Forman et al., Mol. Endocrinol, 4:1293–1301 (1990).
Gabizon et al., Cancer Res. 50:6371–6378 (1990).
Gatti et al., Disease Markers 7:105–112 (1989).
Giguere et al., Nature 330:624–629 (1987).
Goeddel et al., Nucleic Acids Res., 8:4057 (1980).
Goeddel et al., Nature, 281:544 (1979).
Gottlicher et al., Proc. Natl. Acad. Sci USA, 89:4653–4657 (1992).
Hess et al., J. Adv. Enzyme Reg. 7:149 (1968).
Hitzeman et al., J. Biol. Chem. 255:2073 (1980).

Holland et al., *Biochemistry* 17:4900 (1978).
Howell et al., *Blood*, 75:721–729 (1990).
Issemann et al., *Nature*, 347:645–650 (1990).
Itakura et al., *Science*, 198:1056 (1977).
Jones, *Genetics* 85:12 (1977).
Kasai et al., *Cancer Res.* 49: 2603–2605 (1989).
King et al., *Science* 250:121 (1990).
Kingsmanetal., *Gene* 7:141 (1979).
Kitano et al., *Blood*, 77:1625–1626 (1991).
Kliewer et al., *Nature* 358: 771–774 (1992).
Klug et al., *Trends in Biochem. Sci.* 12, 468 (1987).
Kronquist et al., *Prenatal Diagnosis*, 10:739–751 (1990).
Kruse et al., *Tissue Culture*, Academic Press (1973).
Kyte et al., *J. Mol. Biol.*, 157:105–132, (1982).
Lathrop et al., *Proc. Natl. Acad. Sci. USA*. 81:3443–3446 (1984).
Laudet et al., *EMBO*, 11: 1003–1013 (1992).
Marcus, *Academic Press*, 585–599 (1990).
Marsman et al., *Cancer Res.* 48: 6739–6744 (1988).
McBride et al., *J. Exp. Med.* 155:1480–1490 (1982).
McBride et al., *Genomics.* 5:561–573 (1989).
Menger et al., *Blood*, 72:567–572 (1988).
Messing et al., *Third Cleveland Symposium on Macromolecules and Recombinant DNA*, Editor A. Walton, Elsevier, Amsterdam (1981).
Moore, *Development of the Human*, (1982).
Muerhoff et al., *The Journal of Biological Chemistry*, 267:19051–19053 (1992).
Nolta et al., *J. Clinical Investigation*, 90:342–348 (1992).
O'Malley et al., *Mol. Endocrin.* 6: 1359–1361 (1992).
O'Malley et al., *Mol. Endocrin.* 6: 1359–1361 (1992).
Okayama et al., *Mol. Cell Biol.* 3:280 (1983).
Petkovich et al., *Nature* 330:444–450 (1987).
Ranade, *J. Clin. Pharmacol.* 29:685–694 (1989).
Reddy et al., *CRC Crit. Rev. Toxicol.* 12: 1–58 (1983).
Rowley, *J. Clin. Oncol.* 6:194 (1988).
Sambrook et al., *Molecular Cloning: A Laboratory Manual* (Cold Spring Harbor Laboratory Press, Coid Spring Harbor, N.Y.) (1989).
Schmidt et al., *Molecular Endocrinology* 6:1634–1641 (1992).
Schule et al., *Proc. Natl. Acad. Sci. USA* 88:6092–6096 (1991).
Seeburg, *DNA* 1:239 (1982).
Sharif et al., *Cell*, 66:885–893 (1991).
Sher et al., *Biochemistry* 32:5598–5604 (1993).
Short et al., *Nucleir Acids Research*, 16:7583–7600 (1988).
Siebwenlist et al., *Cell*, 20:269 (1980).
Snow and Judd, *Experimental Cell Research*, 171:389–403 (1987).
Staden, *Nucleic Acids Research*, 14:217–231 (1986).
Stinchcomb et al., *Nature*, 282:39 (1979).
Sun, *Hematology, an Atlas and Diagnostic Guide*, I ed, W. B. Saunders, Philadelphia, Pa. (1983).
Tabor and Richardson, *Proc. Natl. Acad. Sci USA*, 86:4076–4080 (1989).
Thomsen et al., *Proc. Natl. Acad. Sci USA* 81:659 (1984).
Tory et al., *Genomics* 13:275–286 (1992).
Truss et al., *Endocrine Rev.* 14: 459479 (1993).
Tschemper et al., *Gene* 10: 157 (1980).
Tsukiyama et al., *Mol. Cell Biol.* 12: 1286–1291 (1992).
Tugwood et al., *EMBO* 11: 433–439 (1992).
Umesono et al., *Cell*, 65:1255–1266 (1991).
Wahli et al., *FASEB*, 5:2243–2249 (1991).
Warren et al., *Cancer Res.* 40: 3641 (1980).

---

What is claimed is:

1. A process of screening a substance for its ability to interact with a human peroxisome proliferator-activated receptor gamma polypeptide, the process comprising the steps of:
   (a) providing a human peroxisome proliferator-activated receptor gamma polypeptide; and
   (b) testing the ability of the substance to interact with the human peroxisome proliferator-activated receptor gamma polypeptide.

2. The process of claim 1 wherein the substance is an agonist.

3. The process of claim 1 wherein the substance is an antagonist.

4. The process of claim 1 wherein the substance has mixed agonist and antagonist properties.

5. The process of claim 1 wherein the substance affects the transcription regulation activity of the human peroxisome proliferator-activated receptor gamma polypeptide.

6. The process of claim 1 wherein the human peroxisome proliferator-activated receptor gamma polypeptide is coupled to a solid support.

7. The process of claim 6 wherein the solid support is selected from the group consisting of agarose beads, polyacrylamide beads and polyacrylic beads.

8. The process of claim 1 wherein the interaction between the substance and the human peroxisome proliferator-activated receptor gamma polypeptide is detected by centrifugation, chromatography, electrophoresis or spectroscopy.

9. The process of claim 1 wherein the interaction between the substance and the human peroxisome proliferator-activated receptor gamma polypeptide is detected by the detection of the production of the polypeptide product encoded by a reporter gene.

10. The process of claim 9 wherein the reporter gene is selected from the group consisting of β-galactosidase, chloramphenicol acetyl transferase and luciferase.

11. The process of claim 1 wherein the substance binds to the human peroxisome proliferator-activated receptor gamma polypeptide.

12. A process of screening a substance for its ability to interact with a human peroxisome proliferator-activated receptor gamma polypeptide, the process comprising the steps of:
   (a) providing a host cell transformed with a polynucleotide, which upon expression, encodes a human peroxisome proliferator-activated receptor gamma polypeptide;
   (b) maintaining the transformed host cell under biological conditions sufficient to allow for the expression of human peroxisome proliferator-activated receptor gamma polypeptide; and
   (c) testing the ability of the substance to interact with the human peroxisome proliferator-activated receptor gamma polypeptide.

13. The process of claim 12 wherein the substance is an agonist.

14. The process of claim 12 wherein the substance is an antagonist.

15. The process of claim 12 wherein the substance has mixed agonist and antagonist properties.

16. The process of claim 12 wherein the substance affects the transcription regulation activity of the human peroxisome proliferator-activated receptor gamma polypeptide.

17. The process of claim 12 wherein the host cell is a prokaryotic or eukaryotic cell.

18. The process of claim 12 further comprising the step of isolating the human peroxisome proliferator-activated receptor gamma polypeptide from the host cell prior to testing the ability of the substance to interact with the human peroxisome proliferator-activated receptor gamma polypeptide.

19. The process of claim 18 wherein the human peroxisome proliferator-activated receptor gamma polypeptide is coupled to a solid support.

20. The process of claim 19 wherein the solid support is selected from the group consisting of agarose beads, polyacrylamide beads and polyacrylic beads.

21. The process of claim 19 wherein the interaction between the substance and the human peroxisome proliferator-activated receptor gamma polypeptide is detected by centrifugation, chromatography, electrophoresis or spectroscopy.

22. The process of claim 19 wherein the interaction between the substance and the human peroxisome proliferator-activated receptor gamma polypeptide is detected by the detection of the production of the polypeptide product encoded by a reporter gene.

23. The process of claim 19 wherein the reporter gene is selected from the group consisting of β-galacrosidase, chloramphenicol, acetyl transferase and luciferase.

24. The process of claim 19 wherein the substance binds to the human peroxisome proliferator-activated receptor gamma polypeptide.

25. A process of screening a substance for its ability to modify the function of the human peroxisome proliferator-activated receptor gamma polypeptide, the process comprising the steps of:
   (a) providing a human peroxisome proliferator-activated receptor gamma polypeptide; and
   (b) testing the ability of the substance to modify the function of the human peroxisome proliferator-activated receptor gamma polypeptide.

26. The process of claim 25 wherein the substance is an agonist.

27. The process of claim 25 wherein the substance is an antagonist.

28. The process of claim 25 wherein the substance has mixed agonist and antagonist properties.

29. The process of claim 25 wherein the substance modifies the transcription regulation activity of the human peroxisome proliferator-activated receptor gamma polypeptide.

30. The process of claim 25 wherein the human peroxisome proliferator-activated receptor gamma polypeptide is coupled to a solid support.

31. The process of claim 30 wherein the solid support is selected from the group consisting of agarose beads, polyacrylamide beads and polyacrylic beads.

* * * * *

SEQUENCE LISTING

```
<160> NUMBER OF SEQ ID NOS: 8

<210> SEQ ID NO 1
<211> LENGTH: 1841
<212> TYPE: DNA
<213> ORGANISM: Homo sapiens
<220> FEATURE:
<221> NAME/KEY: CDS
<222> LOCATION: (179)..(1603)

<400> SEQUENCE: 1
ccgaccttac cccaggcggc cttgacgttg gtcttgtcgg caggagacag caccatggtg    60
ggttctctct gagtctggga attcccgagc ccgagccgca gccgccgcct gggggcttg    120 ggtcggcctc gaggacaccg gagagggcg ccacgccgcc gtggccgcag aaatgacc     178 atg gtt gac aca gag atg cca ttc tgg ccc acc aac ttt ggg atc agc    226
Met Val Asp Thr Glu Met Pro Phe Trp Pro Thr Asn Phe Gly Ile Ser
1               5                   10                  15 tcc gtg gat ctc tcc gta atg gaa gac cac tcc cac tcc ttt gat atc    274
Ser Val Asp Leu Ser Val Met Glu Asp His Ser His Ser Phe Asp Ile
                20                  25                  30 aag ccc ttc act act gtt gac ttc tcc agc att tct act cca cat tac    322
Lys Pro Phe Thr Thr Val Asp Phe Ser Ser Ile Ser Thr Pro His Tyr
            35                  40                  45 gaa gac att cca ttc aca aga aca gat cca gtg gtt gca gat tac aag    370
Glu Asp Ile Pro Phe Thr Arg Thr Asp Pro Val Val Ala Asp Tyr Lys
        50                  55                  60
```

-continued

| | |
|---|---|
| tat gac ctg aaa ctt caa gag tac caa agt gca atc aaa gtg gag cct<br>Tyr Asp Leu Lys Leu Gln Glu Tyr Gln Ser Ala Ile Lys Val Glu Pro<br>65                   70                   75                   80 | 418 |
| gca tct cca cct tat tat tct gag aag act cag ctc tac aat aag cct<br>Ala Ser Pro Pro Tyr Tyr Ser Glu Lys Thr Gln Leu Tyr Asn Lys Pro<br>                   85                   90                   95 | 466 |
| cat gaa gag cct tcc aac tcc ctc atg gca att gaa tgt cgt gtc tgt<br>His Glu Glu Pro Ser Asn Ser Leu Met Ala Ile Glu Cys Arg Val Cys<br>                  100                 105                110 | 514 |
| gga gat aaa gct tct gga ttt cac tat gga gtt cat gct tgt gaa gga<br>Gly Asp Lys Ala Ser Gly Phe His Tyr Gly Val His Ala Cys Glu Gly<br>        115                 120                125 | 562 |
| tgc aag ggt ttc ttc cgg aga aca atc aga ttg aag ctt atc tat gac<br>Cys Lys Gly Phe Phe Arg Arg Thr Ile Arg Leu Lys Leu Ile Tyr Asp<br>130                   135                140 | 610 |
| aga tgt gat ctt aac tgt cgg atc cac aaa aaa agt aga aat aaa tgt<br>Arg Cys Asp Leu Asn Cys Arg Ile His Lys Lys Ser Arg Asn Lys Cys<br>145                   150                155                160 | 658 |
| cag tac tgt cgg ttt cag aaa tgc ctt gca gtg ggg atg tct cat aat<br>Gln Tyr Cys Arg Phe Gln Lys Cys Leu Ala Val Gly Met Ser His Asn<br>                  165                170                175 | 706 |
| gcc atc agg ttt ggg cgg atg cca cag gcc gag aag gag aag ctg ttg<br>Ala Ile Arg Phe Gly Arg Met Pro Gln Ala Glu Lys Glu Lys Leu Leu<br>        180                 185                190 | 754 |
| gcg gag atc tcc agt gat atc gac cag ctg aat cca gag tcc gct gac<br>Ala Glu Ile Ser Ser Asp Ile Asp Gln Leu Asn Pro Glu Ser Ala Asp<br>               195                200                205 | 802 |
| ctc cgg gcc ctg gca aaa cat ttg tat gac tca tac ata aag tcc ttc<br>Leu Arg Ala Leu Ala Lys His Leu Tyr Asp Ser Tyr Ile Lys Ser Phe<br>210                   215                220 | 850 |
| ccg ctg acc aaa gca aag gcg agg gcg atc ttg aca gga aag aca aca<br>Pro Leu Thr Lys Ala Lys Ala Arg Ala Ile Leu Thr Gly Lys Thr Thr<br>225                   230                235                240 | 898 |
| gac aaa tca cca ttc gtt atc tat gac atg aat tcc tta atg atg gga<br>Asp Lys Ser Pro Phe Val Ile Tyr Asp Met Asn Ser Leu Met Met Gly<br>                  245                250                255 | 946 |
| gaa gat aaa atc aag ttc aaa cac atc acc ccc ctg cag gag cag agc<br>Glu Asp Lys Ile Lys Phe Lys His Ile Thr Pro Leu Gln Glu Gln Ser<br>        260                 265                270 | 994 |
| aaa gag gtg gcc atc cgc atc ttt cag ggc tgc cag ttt cgc tcc gtg<br>Lys Glu Val Ala Ile Arg Ile Phe Gln Gly Cys Gln Phe Arg Ser Val<br>               275                280                285 | 1042 |
| gag gct gtg cag gag atc aca gag tat gcc aaa agc att cct ggt ttt<br>Glu Ala Val Gln Glu Ile Thr Glu Tyr Ala Lys Ser Ile Pro Gly Phe<br>290                   295                300 | 1090 |
| gta aat ctt gac ttg aac gac caa gta act ctc ctc aaa tat gga gtc<br>Val Asn Leu Asp Leu Asn Asp Gln Val Thr Leu Leu Lys Tyr Gly Val<br>305                   310                315                320 | 1138 |
| cac gag atc att tac aca atg ctg gcc tcc ttg atg aat aaa gat ggg<br>His Glu Ile Ile Tyr Thr Met Leu Ala Ser Leu Met Asn Lys Asp Gly<br>                  325                330                335 | 1186 |
| gtt ctc ata tcc gag ggc caa ggc ttc atg aca agg gag ttt cta aag<br>Val Leu Ile Ser Glu Gly Gln Gly Phe Met Thr Arg Glu Phe Leu Lys<br>        340                 345                350 | 1234 |
| agc ctg cga aag cct ttt ggt gac ttt atg gag ccc aag ttt gag ttt<br>Ser Leu Arg Lys Pro Phe Gly Asp Phe Met Glu Pro Lys Phe Glu Phe<br>               355                360                365 | 1282 |
| gct gtg aag ttc aat gca ctg gaa tta gat gac agc gac ttg gca ata<br>Ala Val Lys Phe Asn Ala Leu Glu Leu Asp Asp Ser Asp Leu Ala Ile<br>370                   375                380 | 1330 |

-continued

```
ttt att gct gtc att att ctc agt gga gac cgc cca ggt ttg ctg aat      1378
Phe Ile Ala Val Ile Ile Leu Ser Gly Asp Arg Pro Gly Leu Leu Asn
385                 390                 395                 400 gtg aag ccc att gaa gac att caa gac aac ctg cta caa gcc ctg gag      1426
Val Lys Pro Ile Glu Asp Ile Gln Asp Asn Leu Leu Gln Ala Leu Glu
                405                 410                 415 ctc cag ctg aag ctg aac cac cct gag tcc tca cag ctg ttt gcc aag      1474
Leu Gln Leu Lys Leu Asn His Pro Glu Ser Ser Gln Leu Phe Ala Lys
            420                 425                 430 ctg ctc cag aaa atg aca gac ctc aga cag att gtc acg gaa cac gtg      1522
Leu Leu Gln Lys Met Thr Asp Leu Arg Gln Ile Val Thr Glu His Val
        435                 440                 445 cag cta ctg cag gtg atc aag aag acg gag aca gac atg agt ctt cac      1570
Gln Leu Leu Gln Val Ile Lys Lys Thr Glu Thr Asp Met Ser Leu His
    450                 455                 460 ccg ctc ctg cag gag atc tac aag gac ttg tac tagcagagag tcctgagcca    1623
Pro Leu Leu Gln Glu Ile Tyr Lys Asp Leu Tyr
465                 470                 475 ctgccaacat ttcccttctt ccagttgcac tattctgagg gaaaatctga ccataagaaa    1683
tttactgtga aaaagcgttt taaaaagaaa agggtttaga atatgatcta ttttatgcat    1743
attgtttata agacacatt tacaatttac ttttaatatt aaaaattacc atattatgaa     1803
attgcaaaaa aaaaaaaaaa aaaaaaaaaa aaaaaaaa                            1841
```

<210> SEQ ID NO 2
<211> LENGTH: 475
<212> TYPE: PRT
<213> ORGANISM: Homo sapiens

<400> SEQUENCE: 2

```
Met Val Asp Thr Glu Met Pro Phe Trp Pro Thr Asn Phe Gly Ile Ser
1               5                   10                  15

Ser Val Asp Leu Ser Val Met Glu Asp His Ser His Ser Phe Asp Ile
                20                  25                  30

Lys Pro Phe Thr Thr Val Asp Phe Ser Ser Ile Ser Thr Pro His Tyr
            35                  40                  45

Glu Asp Ile Pro Phe Thr Arg Thr Asp Pro Val Val Ala Asp Tyr Lys
        50                  55                  60

Tyr Asp Leu Lys Leu Gln Glu Tyr Gln Ser Ala Ile Lys Val Glu Pro
65                  70                  75                  80

Ala Ser Pro Pro Tyr Tyr Ser Glu Lys Thr Gln Leu Tyr Asn Lys Pro
                85                  90                  95

His Glu Glu Pro Ser Asn Ser Leu Met Ala Ile Glu Cys Arg Val Cys
            100                 105                 110

Gly Asp Lys Ala Ser Gly Phe His Tyr Gly Val His Ala Cys Glu Gly
        115                 120                 125

Cys Lys Gly Phe Phe Arg Arg Thr Ile Arg Leu Lys Leu Ile Tyr Asp
    130                 135                 140

Arg Cys Asp Leu Asn Cys Arg Ile His Lys Lys Ser Arg Asn Lys Cys
145                 150                 155                 160

Gln Tyr Cys Arg Phe Gln Lys Cys Leu Ala Val Gly Met Ser His Asn
                165                 170                 175

Ala Ile Arg Phe Gly Arg Met Pro Gln Ala Glu Lys Glu Lys Leu Leu
            180                 185                 190

Ala Glu Ile Ser Ser Asp Ile Asp Gln Leu Asn Pro Glu Ser Ala Asp
        195                 200                 205
```

```
Leu Arg Ala Leu Ala Lys His Leu Tyr Asp Ser Tyr Ile Lys Ser Phe
    210                 215                 220

Pro Leu Thr Lys Ala Lys Ala Arg Ala Ile Leu Thr Gly Lys Thr Thr
225                 230                 235                 240

Asp Lys Ser Pro Phe Val Ile Tyr Asp Met Asn Ser Leu Met Met Gly
                245                 250                 255

Glu Asp Lys Ile Lys Phe Lys His Ile Thr Pro Leu Gln Glu Gln Ser
            260                 265                 270

Lys Glu Val Ala Ile Arg Ile Phe Gln Gly Cys Gln Phe Arg Ser Val
        275                 280                 285

Glu Ala Val Gln Glu Ile Thr Glu Tyr Ala Lys Ser Ile Pro Gly Phe
290                 295                 300

Val Asn Leu Asp Leu Asn Asp Gln Val Thr Leu Leu Lys Tyr Gly Val
305                 310                 315                 320

His Glu Ile Ile Tyr Thr Met Leu Ala Ser Leu Met Asn Lys Asp Gly
                325                 330                 335

Val Leu Ile Ser Glu Gly Gln Gly Phe Met Thr Arg Glu Phe Leu Lys
            340                 345                 350

Ser Leu Arg Lys Pro Phe Gly Asp Phe Met Glu Pro Lys Phe Glu Phe
        355                 360                 365

Ala Val Lys Phe Asn Ala Leu Glu Leu Asp Asp Ser Asp Leu Ala Ile
    370                 375                 380

Phe Ile Ala Val Ile Ile Leu Ser Gly Asp Arg Pro Gly Leu Leu Asn
385                 390                 395                 400

Val Lys Pro Ile Glu Asp Ile Gln Asp Asn Leu Leu Gln Ala Leu Glu
                405                 410                 415

Leu Gln Leu Lys Leu Asn His Pro Glu Ser Ser Gln Leu Phe Ala Lys
            420                 425                 430

Leu Leu Gln Lys Met Thr Asp Leu Arg Gln Ile Val Thr Glu His Val
        435                 440                 445

Gln Leu Leu Gln Val Ile Lys Lys Thr Glu Thr Asp Met Ser Leu His
450                 455                 460

Pro Leu Leu Gln Glu Ile Tyr Lys Asp Leu Tyr
465                 470                 475

<210> SEQ ID NO 3
<211> LENGTH: 41
<212> TYPE: DNA
<213> ORGANISM: Homo sapiens

<400> SEQUENCE: 3
actagtgcgg ccgcctaggc ctcgagtttt tttttttttt t                    41

<210> SEQ ID NO 4
<211> LENGTH: 23
<212> TYPE: DNA
<213> ORGANISM: Homo sapiens
<220> FEATURE:
<221> NAME/KEY: misc_feature
<222> LOCATION: (3)..(3)
<223> OTHER INFORMATION: y=c or t
<220> FEATURE:
<221> NAME/KEY: misc_feature
<222> LOCATION: (6)..(6)
<223> OTHER INFORMATION: r= a or g
<220> FEATURE:
<221> NAME/KEY: misc_feature
<222> LOCATION: (9)..(9)
<223> OTHER INFORMATION: n= g, a, c or t
```

```
<220> FEATURE:
<221> NAME/KEY: misc_feature
<222> LOCATION: (12)..(12)
<223> OTHER INFORMATION: y=c or t
<220> FEATURE:
<221> NAME/KEY: misc_feature
<222> LOCATION: (15)..(15)
<223> OTHER INFORMATION: r= a or g
<220> FEATURE:
<221> NAME/KEY: misc_feature
<222> LOCATION: (18)..(18)
<223> OTHER INFORMATION: n=g, a, c or t
<220> FEATURE:
<221> NAME/KEY: misc_feature
<222> LOCATION: (21)..(21)
<223> OTHER INFORMATION: y= c or t

<400> SEQUENCE: 4
tgygarggnt gyaarggntt ytt                                           23

<210> SEQ ID NO 5
<211> LENGTH: 8
<212> TYPE: PRT
<213> ORGANISM: Homo sapiens

<400> SEQUENCE: 5

Cys Glu Gly Cys Lys Gly Phe Phe
1               5

<210> SEQ ID NO 6
<211> LENGTH: 19
<212> TYPE: DNA
<213> ORGANISM: Homo sapiens

<400> SEQUENCE: 6
acgtgacctt tgtcctggt                                                19

<210> SEQ ID NO 7
<211> LENGTH: 6
<212> TYPE: DNA
<213> ORGANISM: Homo sapiens

<400> SEQUENCE: 7 tgacct                                                              6

<210> SEQ ID NO 8
<211> LENGTH: 15
<212> TYPE: PRT
<213> ORGANISM: Homo sapiens

<400> SEQUENCE: 8

Cys Glu Gly Cys Lys Gly Phe Phe Arg Arg Thr Ile Arg Leu Lys
1               5                   10                  15
```